(12) United States Patent
Muehleisen et al.

(10) Patent No.: US 9,939,343 B2
(45) Date of Patent: Apr. 10, 2018

(54) ACOUSTIC BUILDING INFILTRATION MEASUREMENT SYSTEM

(71) Applicant: UCHICAGO ARGONNE, LLC, Chicago, IL (US)

(72) Inventors: Ralph T. Muehleisen, Oak Park, IL (US); Ganesh Raman, Glenview, IL (US)

(73) Assignee: UChicago Argonne, LLC, Chicago, IL (US)

( * ) Notice: Subject to any disclaimer, the term of this patent is extended or adjusted under 35 U.S.C. 154(b) by 565 days.

(21) Appl. No.: 14/503,071

(22) Filed: Sep. 30, 2014

(65) Prior Publication Data
US 2016/0091387 A1 Mar. 31, 2016

(51) Int. Cl.
| | | |
|---|---|---|
| G01M 3/24 | (2006.01) | |
| G01N 29/024 | (2006.01) | |
| G01N 29/46 | (2006.01) | |
| G01N 29/06 | (2006.01) | |

(52) U.S. Cl.
CPC ............ *G01M 3/24* (2013.01); *G01N 29/024* (2013.01); *G01N 29/0663* (2013.01); *G01N 29/46* (2013.01); *G01N 2291/011* (2013.01)

(58) Field of Classification Search
CPC .. G01N 29/024; G01N 29/46; G01N 29/0663; G01N 2291/011; G01M 3/24
See application file for complete search history.

(56) References Cited

U.S. PATENT DOCUMENTS

| | | | | |
|---|---|---|---|---|
| 5,161,408 A | * | 11/1992 | McRae | G01M 3/38 250/334 |
| 5,675,506 A | * | 10/1997 | Savic | F17D 5/06 702/51 |
| 2010/0195842 A1 | * | 8/2010 | Sibbald | H04R 1/1083 381/71.6 |
| 2011/0120222 A1 | * | 5/2011 | Scholte | G01H 3/125 73/603 |

OTHER PUBLICATIONS

Bai, "Application of BEM (boundary element method)-based acoustic holography to radiation analysis of sound sources with arbitrarily shaped geometries," Journal of the Acoustical Society of America, vol. 92, No. 1, Jul. 1992, pp. 533-549.
Chelliah et al., "Draft: Leakage detection techniques using nearfield acoustic holography," ASME, Aug. 2014, 15 pages.
Maynard et al., "Nearfield acoustic holography: I. Theory of generalized holography and the development of NAH," Journal of the Acoustical Society of America, vol. 78, No. 4, Oct. 1985, pp. 1395-1413.
Sarkissian, "Method of superposition applied to patch near-field acoustic holography," Journal of the Acoustical Society of America, vol. 188, No. 2, Aug. 2005, pp. 671-678.
Wang and Wu, "Helmholtz equation—least-squarese method for reconstructing the acoustic pressure field," Journal of the Acoustical Society of America, vol. 102, No. 4, Oct. 1997, pp. 2020-2032.

\* cited by examiner

*Primary Examiner* — Bryan Bui
(74) *Attorney, Agent, or Firm* — Foley & Lardner LLP

(57) ABSTRACT

Systems and methods of detecting and identifying a leak from a container or building. Acoustic pressure and velocity are measured. Acoustic properties are acquired from the measured values. The acoustic properties are converted to infiltration/leakage information. Nearfield Acoustic Holography (NAH) may be one method to detect the leakages from a container by locating the noise sources.

19 Claims, 20 Drawing Sheets

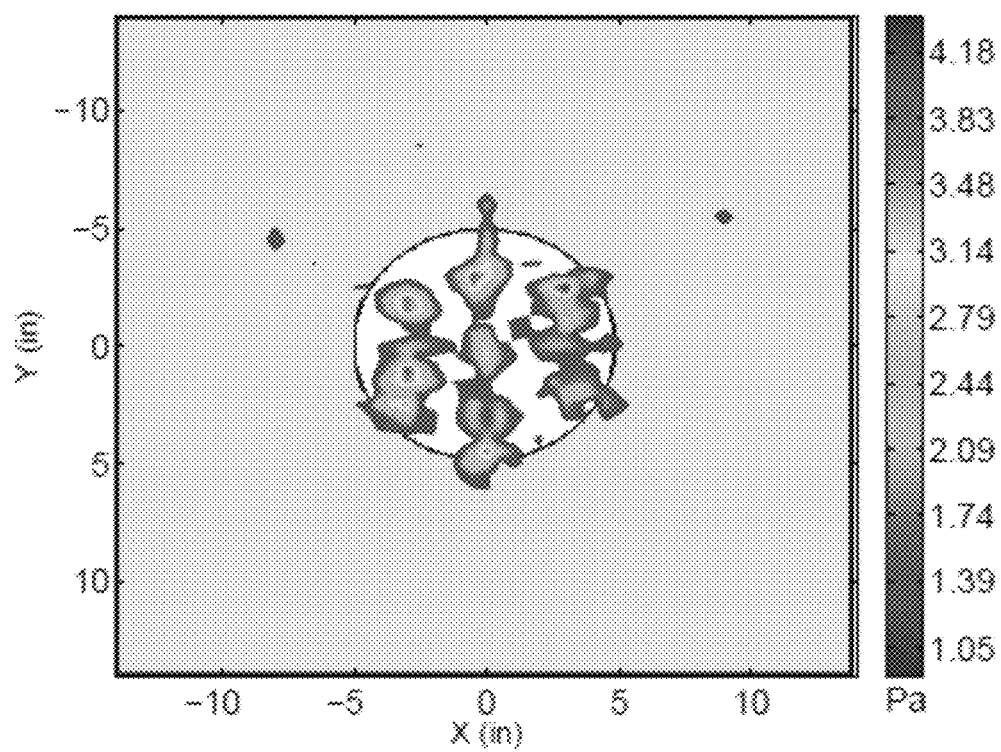
Figure 4 (a) FFT

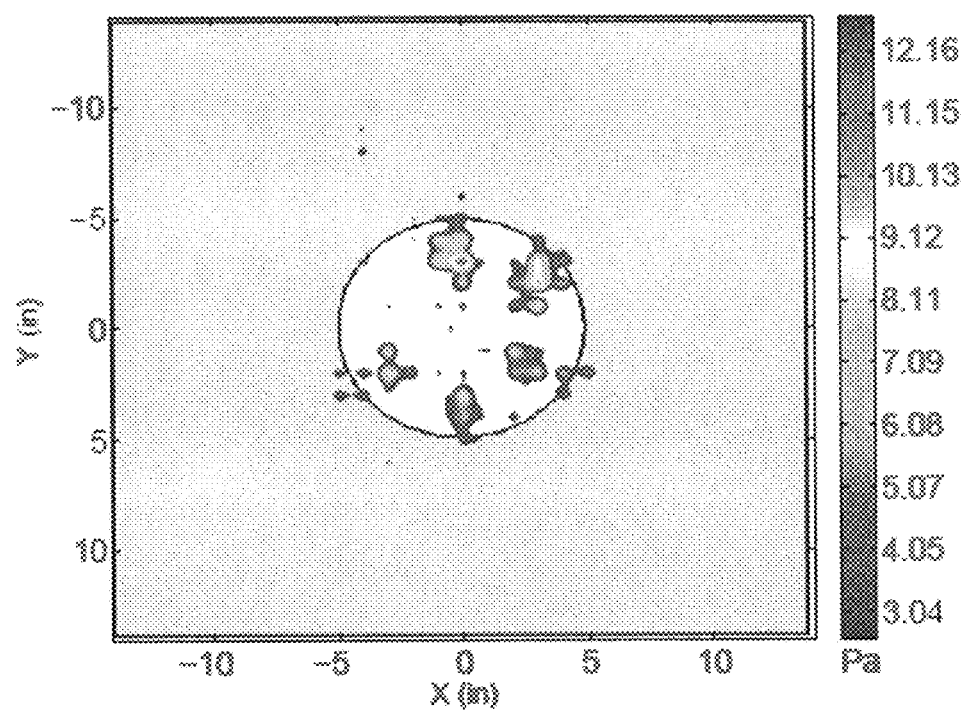
Figure 4 (b) BEM

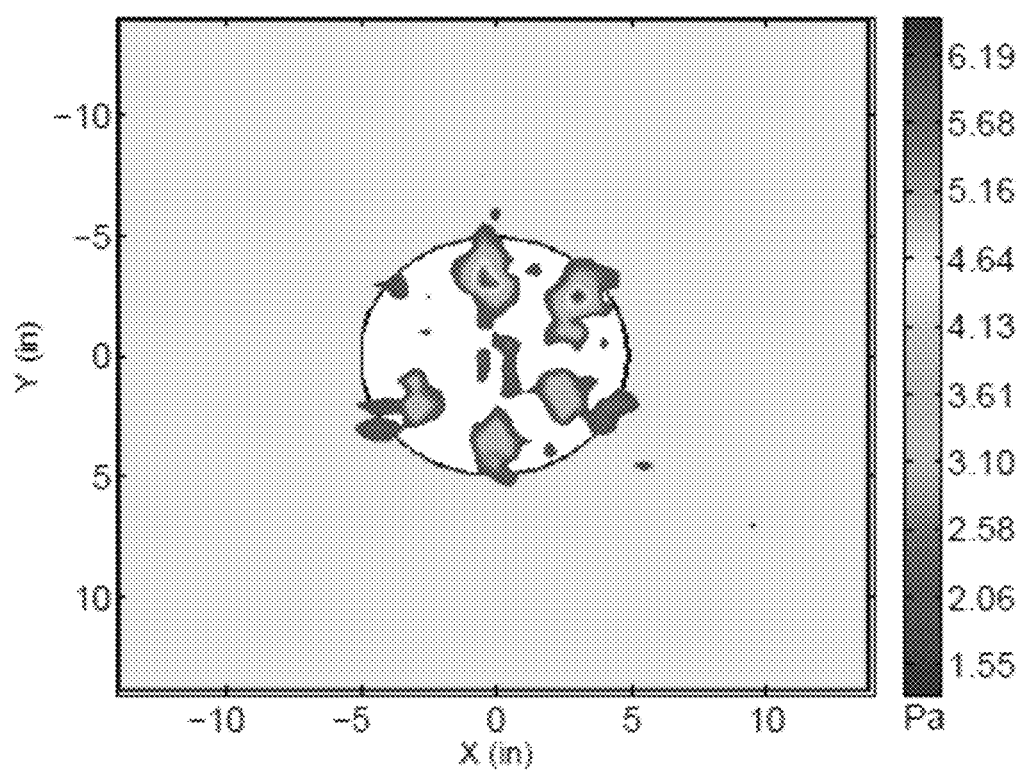
Figure 4(c) ESM

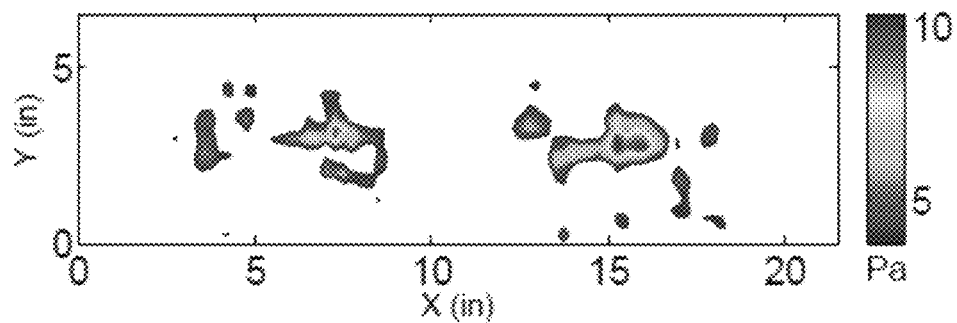
Figure 5 (a) FFT
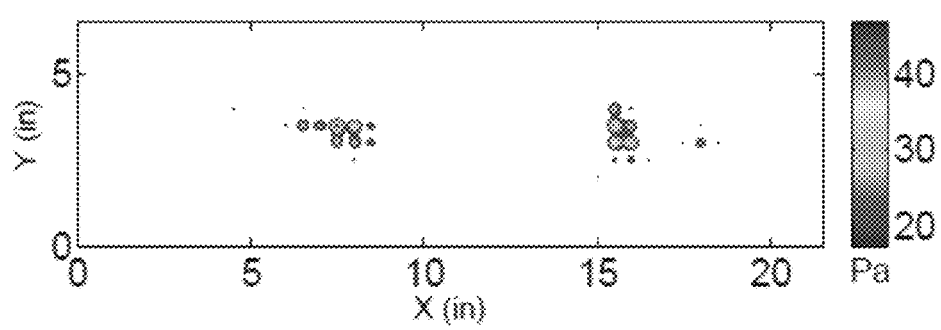
Figure 5 (b) BEM
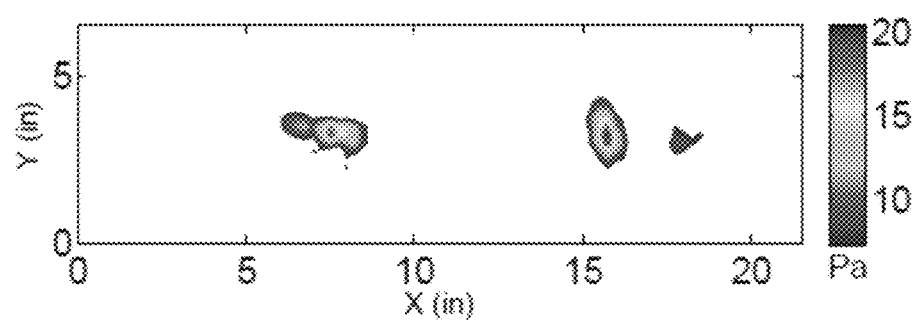
Figure 5 (c) ESM

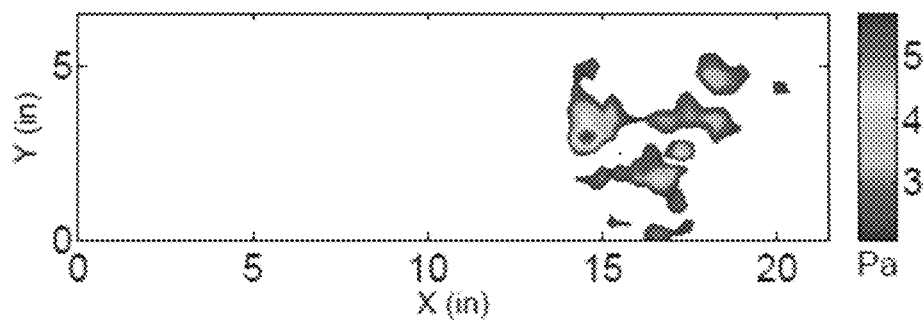
Figure 6 (a) FFT
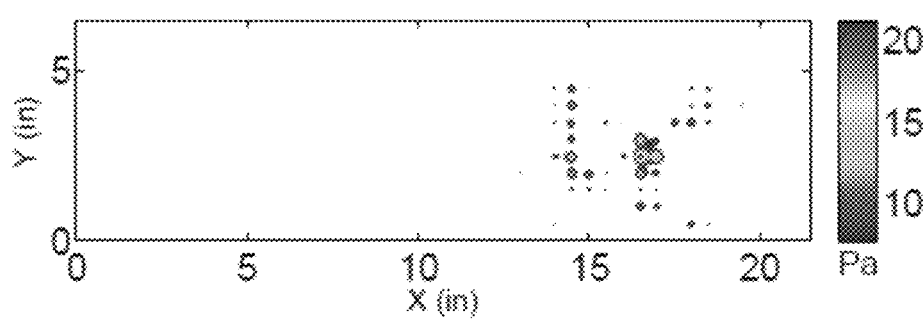
Figure 6 (b) BEM
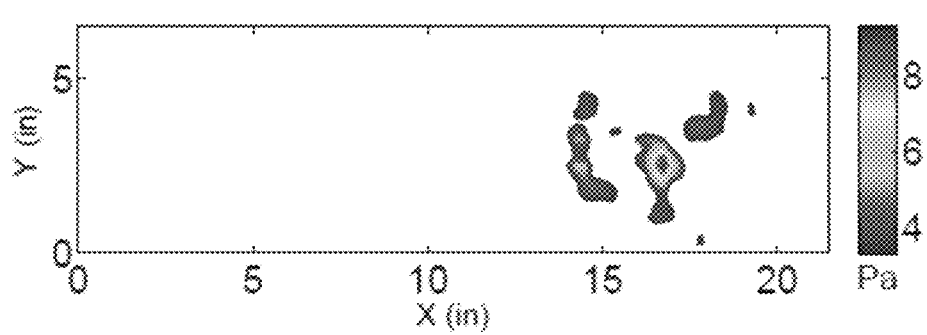
Figure 6 (c) ESM

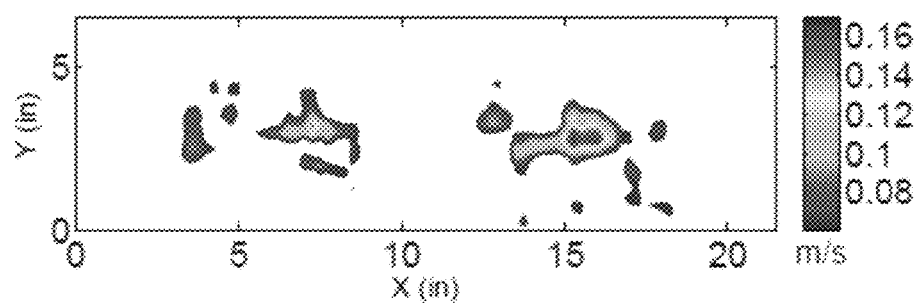
Figure 7 (a) FFT
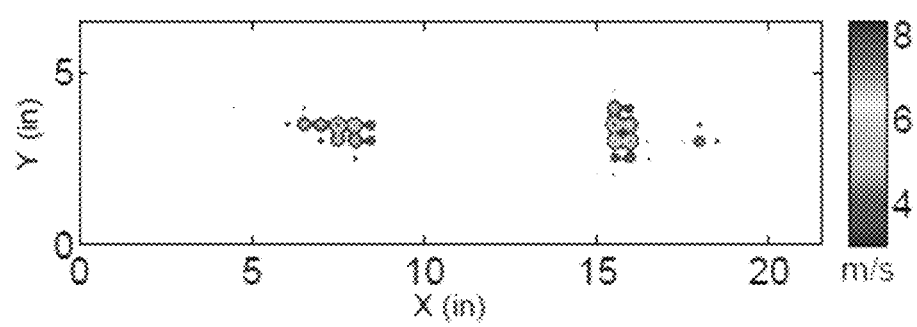
Figure 7 (b) BEM
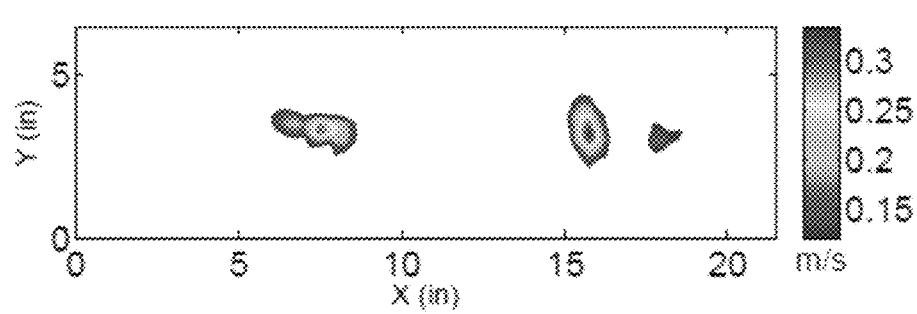
Figure 7 (c) ESM

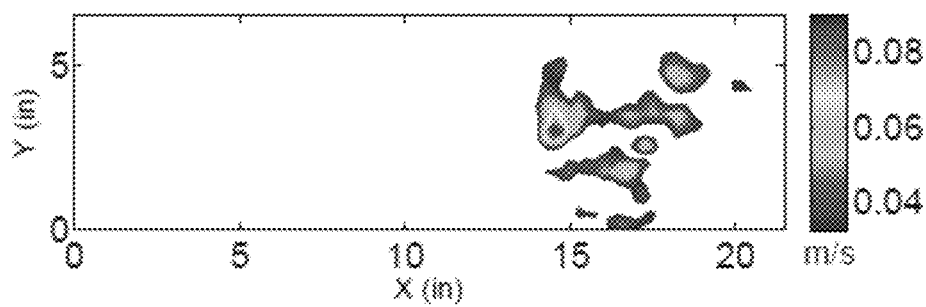
Figure 8 (a) FFT
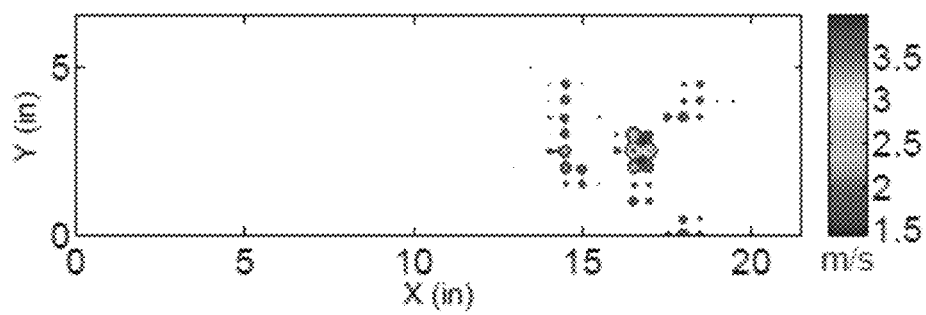
Figure 8 (b) BEM
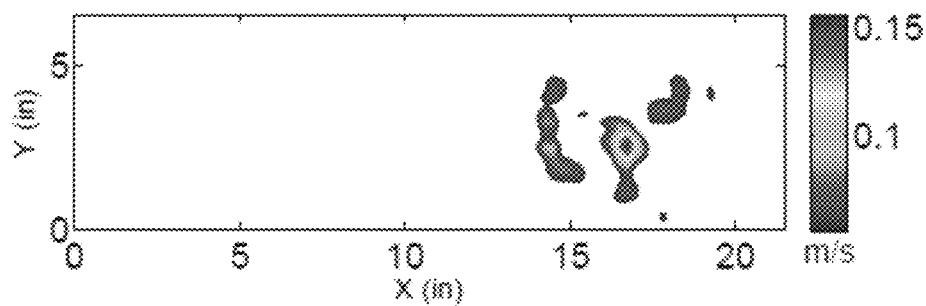
Figure 8 (c) ESM

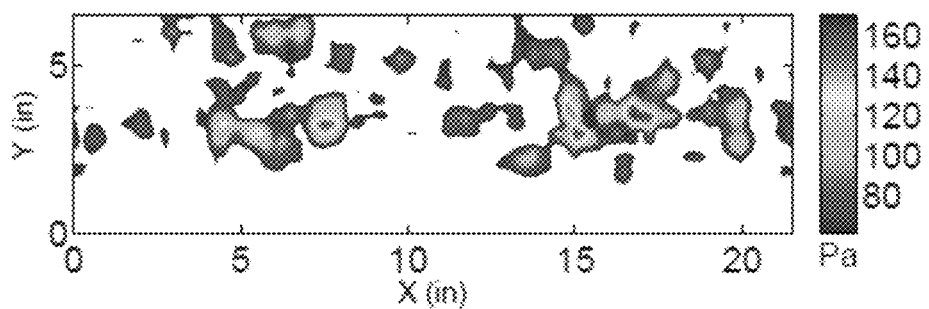
Figure 9 (a) FFT
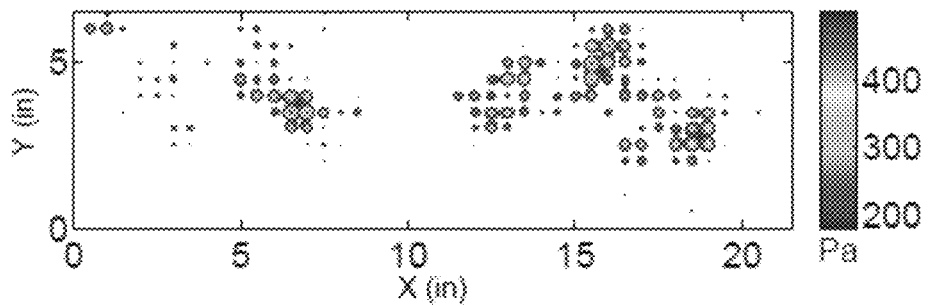
Figure 9 (b) BEM
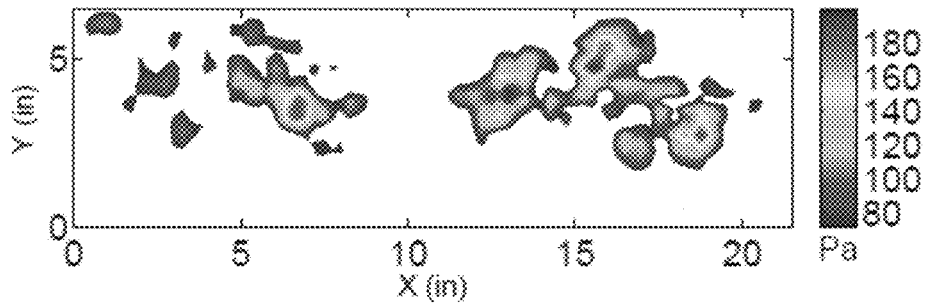
Figure 9 (c) ESM

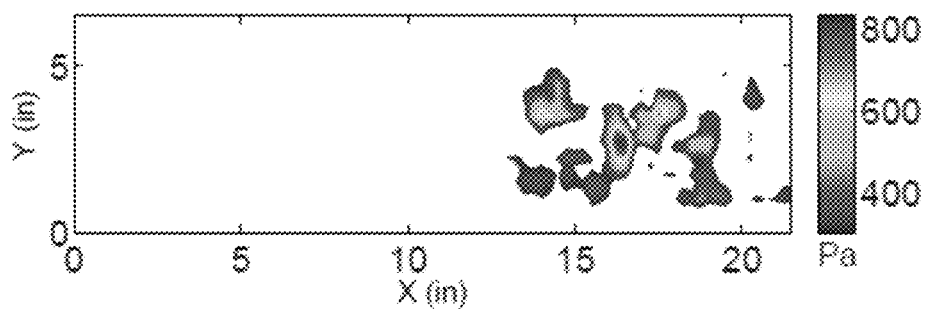
Figure 10 (a) FFT
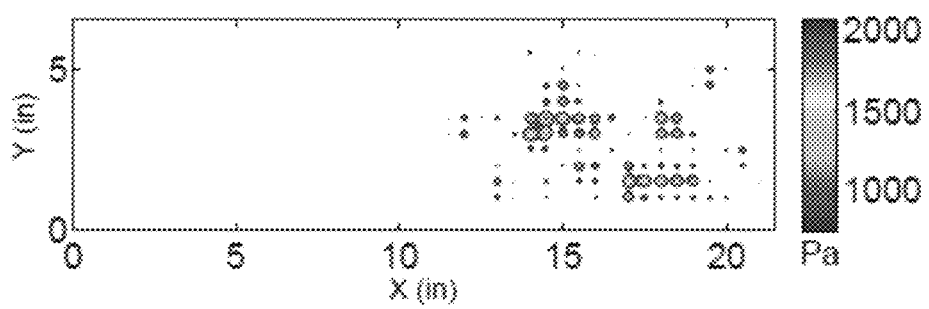
Figure 10 (b) BEM
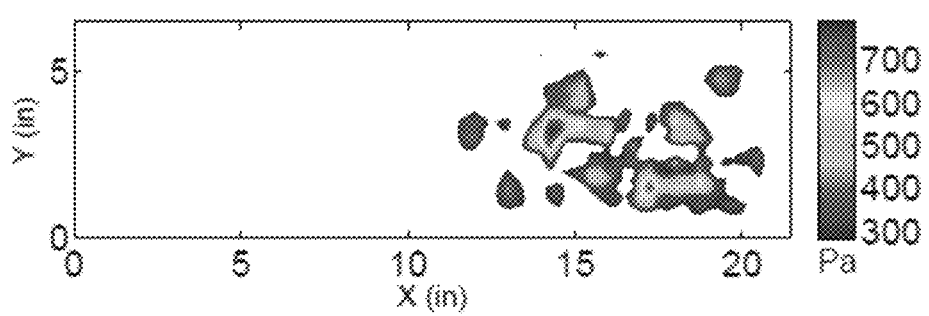
Figure 10 (c) ESM

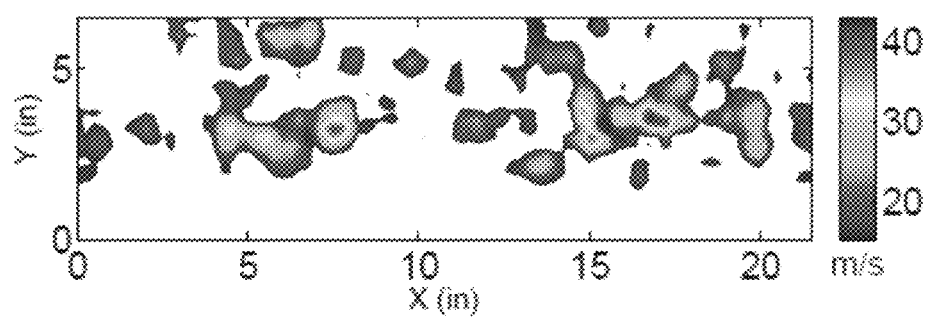
Figure 11 (a) FFT
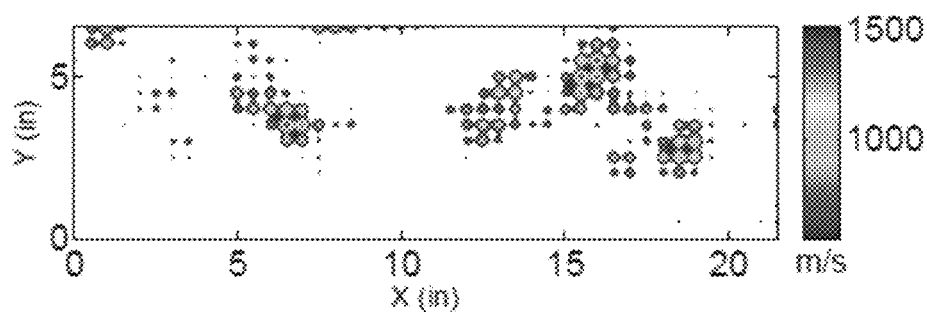
Figure 11 (b) BEM
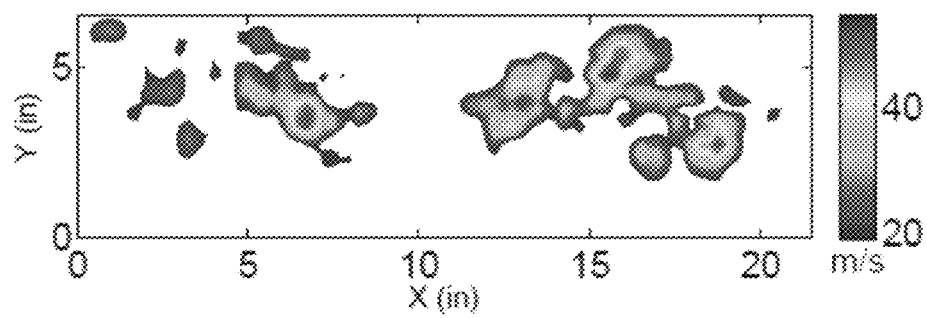
Figure 11 (c) ESM

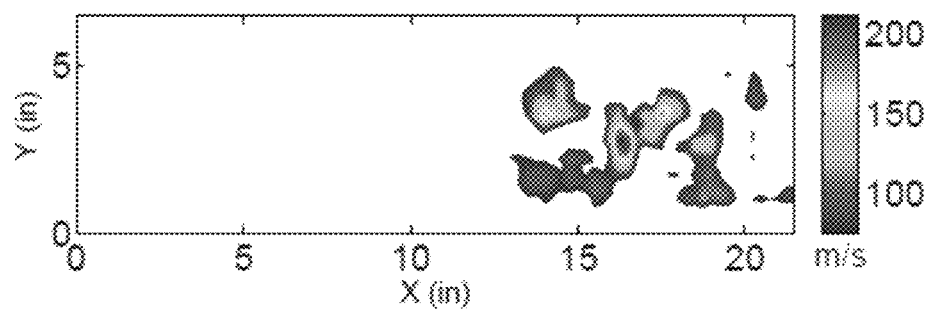
Figure 12 (a) FFT
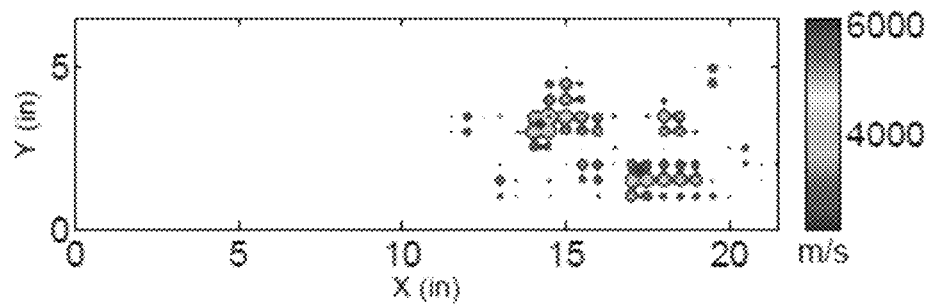
Figure 12 (b) BEM
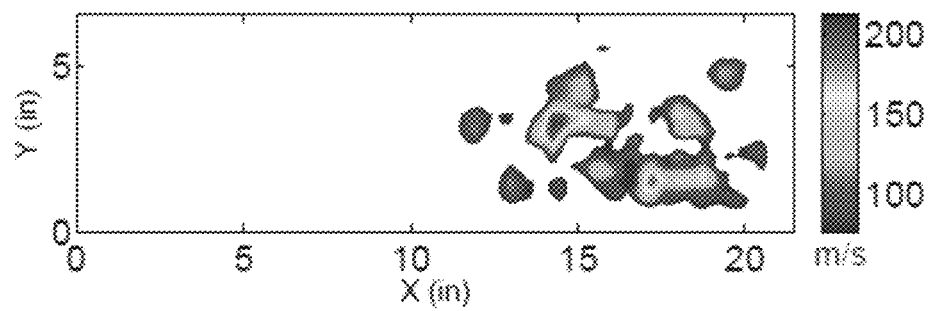
Figure 12 (c) ESM

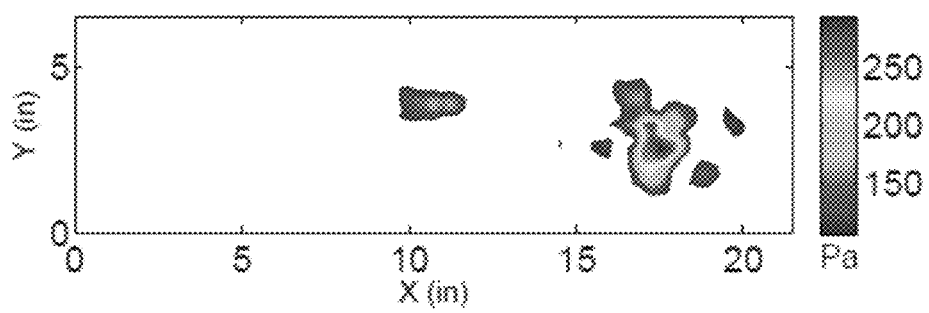
Figure 13 (a) $ABS(p_S)$
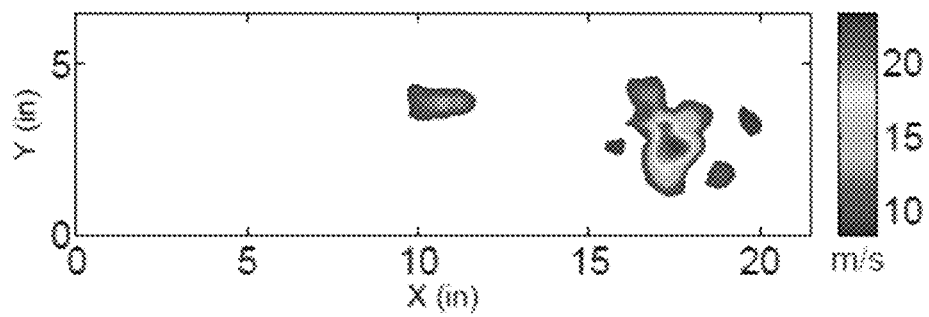
Figure 13 (b) $ABS(V_S)$

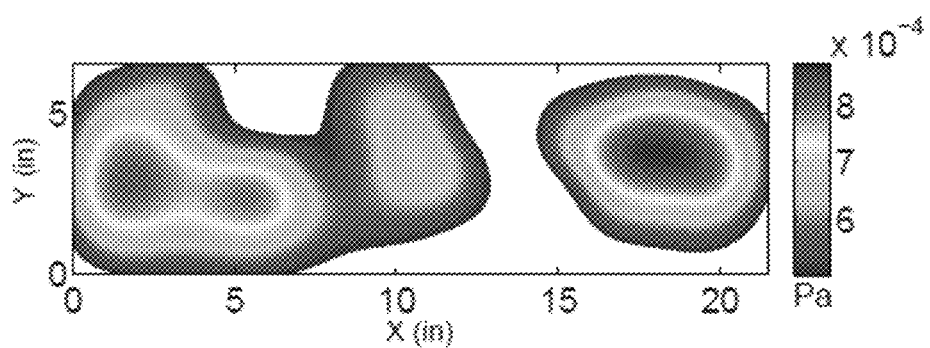
Figure 14   (a) ABS($p_s$)
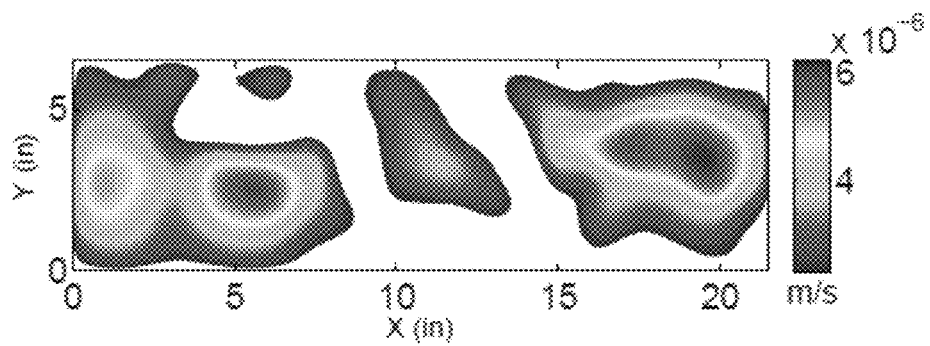
Figure 14   (b) ABS($V_z$)

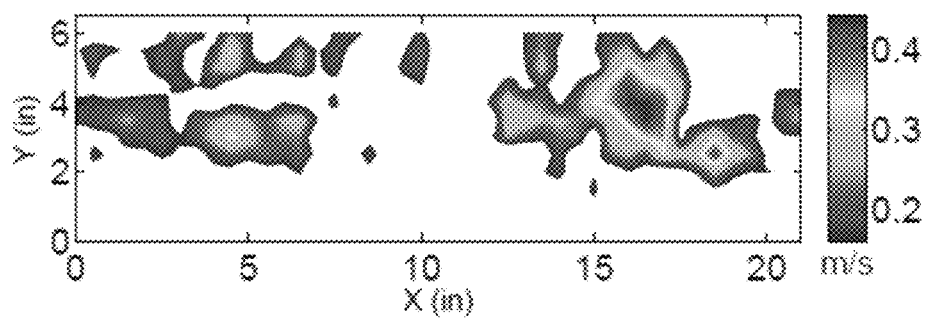
Figure 15 (a) FFT
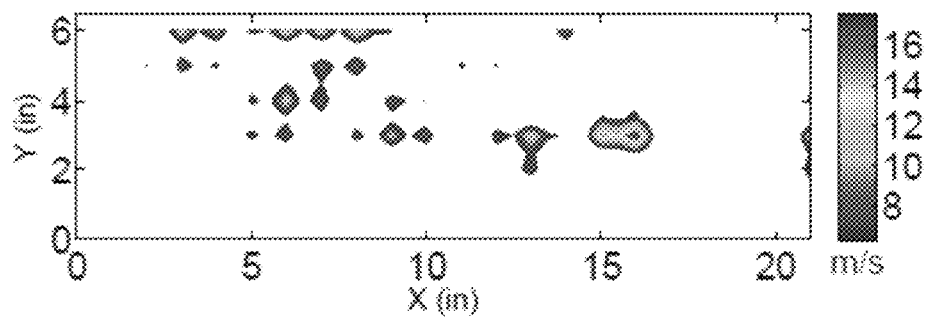
Figure 15 (b) BEM
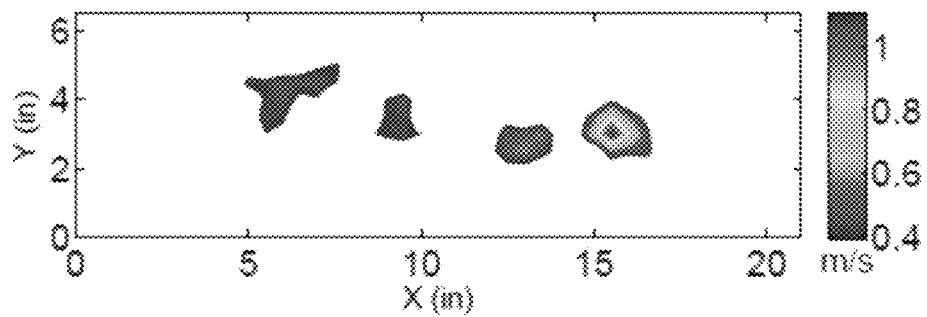
Figure 15 (c) ESM

ACOUSTIC BUILDING INFILTRATION MEASUREMENT SYSTEM

STATEMENT OF GOVERNMENT INTEREST

The United States Government has rights in the invention described herein pursuant to Contract No. DE-AC02-06CH11357 between the United States Department of Energy and UChicago Argonne, LLC, as operator of Argonne National Laboratory.

FIELD OF THE INVENTION

The present invention generally relates to leakage or infiltration detection. More specifically, the present invention relates to systems and methods of identifying and converting acoustic properties to infiltration or leakage information.

BACKGROUND OF THE INVENTION

Building air infiltration, the uncontrolled leakage of air in and out of buildings, accounts for over 30% of total heating load of commercial buildings in the US. Measuring the infiltration in commercial buildings is difficult because of the physical size and measurements cannot be made during construction which means sealing the building becomes more difficult and expensive.

Two methods for measuring building infiltration are currently used: pressurization testing and tracer gas testing. Pressurization testing works by pressurizing an entire building or building section with fans and measuring the air flow through and pressure difference across the envelope. This method works well for small buildings but is impractical for large buildings. Further, the entire building envelope must be constructed before the method can be used. The tracer gas method works by introducing a gas into a room at a known rate and measuring the amount of time for the gas concentration to be reduced through infiltration and exfiltration. The tracer technique can take a very long time (especially on buildings with low infiltration), is more difficult to apply in large buildings, and also needs a completed building enclosure to utilize.

Others have attempted to correlate sound transmission loss to infiltration rates with limited success. While correlations do exist, they are specific to the exact details of wall construction and infiltration location so one cannot develop correlations on one building and use them on another and hence the method cannot be used as a general method for measuring infiltration. Further, there is no general method on how to estimate the correlations without actual measurement of the building (i.e. from drawings and computer models).

Leakages in a gas-storing containers and air-conditioned buildings are serious safety and economic problem to the society. However, the present leakage detection methods such as smoke stick method are not very effective and involves a lot of human resource.

SUMMARY OF THE INVENTION

One embodiment of the invention relates to A method of detecting leakage. Sound is emitted from an electroacoustic transducer positioned within a structure. Internal pressure of the emitted sound within the structure is measured. Sound external to the structure is detected. External pressure and external velocity of the detected sound external to the device is measured. A leak in the structure is determined.

Another implementation relates to a system for detecting leakage. An electroacoustic transducer is configured to emit an acoustic wave having a phase, frequency and amplitude, the transducer in communication with a computer to provide the phase, frequency, and amplitude of the emitted acoustic wave. An acoustic transducer system is configured to detect acoustic pressure and acoustic velocity Another implementation relates to a computer system for leakage detection. An electroacoustic transducer is configured to emit an acoustic wave having a phase, frequency and amplitude, the transducer in communication with a computer to provide the phase, frequency, and amplitude of the emitted acoustic wave. A microphone array is configured to receive the acoustic wave, the microphone array in communication with the computer providing acoustic velocity and acoustic pressure data to the computer. The computer includes a processor and a tangible computer-readable medium operatively connected to the processor and including computer code configured to determine from the array acoustic velocity and pressure data a pressure associated with each of a plurality of points.

Additional features, advantages, and embodiments of the present disclosure may be set forth from consideration of the following detailed description, drawings, and claims. Moreover, it is to be understood that both the foregoing summary of the present disclosure and the following detailed description are exemplary and intended to provide further explanation without further limiting the scope of the present disclosure claimed.

BRIEF DESCRIPTION OF THE DRAWINGS

The foregoing and other objects, aspects, features, and advantages of the disclosure will become more apparent and better understood by referring to the following description taken in conjunction with the accompanying drawings, in which:

FIGS. 4A-C illustrates the results of a qualification test for various NAH algorithms, contours, algorithms, contours of $p_s$ for the input frequency f=5004 Hz for (A) FFT, (B) BEM and (C) ESM.

FIGS. 5A-C are graphs of reconstructed absolute acoustic pressure using various algorithms, insert 1, f=5004 Hz for (A) FFT, (B) BEM and (C) ESM.

FIGS. 6A-C are graphs of reconstructed absolute acoustic pressure using various algorithms insert 11, f=5004 Hz3 for (A) FFT, (B) BEM and (C) ESM.

FIGS. 7A-C are graphs of reconstructed absolute particle velocity using various algorithms insert I, f=5004 Hz for (A) FFT, (B) BEM and (C) ESM.

FIGS. 8A-C are graphs of reconstructed absolute particle velocity using algorithms, insert II, f=5004 Hz for (A) FFT, (B) BEM and (C) ESM FIGS. 9A-C are graphs of reconstructed absolute acoustic pressure using various algorithms, insert I, f=317 Hz for (A) FFT, (B) BEM and (C) ESM.

FIGS. 10A-C are graphs of reconstructed absolute acoustic pressure using various algorithms, insert II, f=317 Hz for (A) FFT, (B) BEM and (C) ESM.

FIGS. 11A-C are graphs of reconstructed absolute particle velocity using various algorithms, insert I, f=317 Hz for (A) FFT, (B) BEM and (C) ESM.

FIG. 12A-C are graphs of reconstructed absolute particle velocity using various algorithms, insert II, f=317 Hz for (A) FFT, (B) BEM and (C) ESM.

FIGS. 13A-B is a graph of acoustic pressure (13A) and particle velocity (13B) using ESM, insert II, f=1098 Hz.

FIGS. 14A-B are graphs of acoustic pressure (14A) and particle velocity (14B) using ESM-GCV, f=317 Hz; Dx=0:25 in FIGS. 15A-C are graphs of reconstructed absolute particle velocity calculated with reduced resolution (Dx=0:5 in) using various algorithms, insert I, f=317 Hz for (A) FFT, (B) BEM and (C) ESM.

DETAILED DESCRIPTION OF THE PREFERRED EMBODIMENTS

Figure 1A:
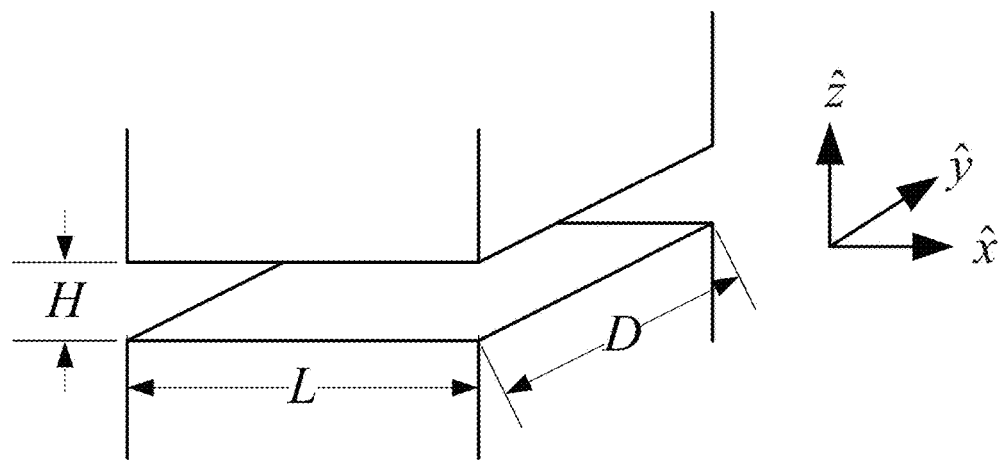
FIG. 1A Illustrates the geometry of a crack, such as in building infiltration, that is H in height, L in length, and D in depth.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and made part of this disclosure.

One implementation provides methods and systems for implementing an Acoustic Building Infiltration Measurement System (ABIMS). ABIMS is a device which uses acoustic methods for measuring building air infiltration (or leakage). It should be appreciated that whether the concern or reality of a structure is leakage from the structure to the outside environment or infiltration into the structure from the outside environment, the concepts described herein are applicable, although in the context of this disclosure only leakage or infiltration may be described for a given implementation. An ABIMS converts acoustic properties to leakage information. In one implementation, the present invention relates to a system for and methods of 1) measuring acoustic pressure and velocity, 2) acquiring acoustic properties such as acoustic impedance, or porous media properties (tortuosity, complex density, complex compressibility, flow resistivity, viscous permeability, etc) from the pressure and velocity measurements, and 3) converting the acoustic properties to infiltration/leakage information.

In building science, infiltration is typically referred to as a function of an infiltration flow coefficient and a pressure difference modified by a power. Specifically, it is typical to express the relationship between infiltration airflow (denoted as Q with units of m³/s), and the pressure difference between the building interior and exterior (denoted as ΔP with units of Pa) by a power law of the form (Sherman, 1992):

$$Q = C_L (\Delta P)^n. \tag{1}$$

where $C_L$ is the infiltration flow coefficient and n is the infiltration exponent. Typically, both C and n depend upon the geometry of the crack or cracks through which the infiltration is occurring. Analytic expressions for C and n for Eqn. (1) are desired for some simple geometries. Further determine the infiltration, it is necessary to determine infiltration flow coefficient.

Measuring Acoustic Pressure and Velocity

It should be appreciated that several techniques can be utilized with the above method to provide the measurement of acoustic pressure and velocity. When velocity is referred to herein, such is the particle velocity not the speed of sound. Systems for use in measuring the acoustic pressure include, but are not limited to: transducers, including pressure sensors such as electret, condenser, moving coil, or piezoelectric microphones, and piezoelectric microphones. Systems for use in measuring the acoustic particle velocity include, but are: conversion of sound pressure measured by pressure sensors as is used in two microphone sound intensity probes, ribbon microphones, MEMS based probes such as that sold by Microflow Technologies®, particle image velocimetry, and Doppler measurement systems such as Laser Doppler Vibrometry (LDV) or Laser Doppler Anemometry (LDA).

One implementation of the present invention utilizes Nearfield Acoustic Holography ("NAH") to measure the acoustic pressure and velocity. Once the acoustic pressure and velocity are determined, that sound leakage information is converted to a static pressure flow equivalent using basic equations derived from fluid mechanics. From that, standard infiltration measures are computed. In other implementations, the system and methods can utilize any other technique that can measure both the pressure amplitude and particle velocity of sound at specific locations on the building enclosure surface.

Conformal NAH is based on Fourier transform and convolution, such as utilizing fast Fourier transform ("FFT"). These FFT based methods pose constraints on the geometry and distribution of sources and transducers (microphones in most of the cases). These limitations created the requirement for modern NAH algorithms based on numerical methods to solve the linear acoustic equations. NAH works based on the data measured on a hologram surface to reconstruct the acoustic quantities in the three dimensional domain using the boundary integral form of Helmholtz equation. Therefore, a natural choice of numerical method was the boundary element method (BEM). Another simple yet powerful NAH algorithm called equivalent source model ("ESM") (also called wave superposition method) was used in many of the recent studies. Later, Bai introduced a beamformer-like ESM algorithm in time domain and tested it experimentally by prior researchers. Miller et al and Valdivia et al compared the two algorithms (BEM and ESM) extensively. The BEM algorithm is usually considered as more accurate method. However, the ESM algorithm is easier to implement and requires less CPU time compared to BEM. A hybrid method by combining the BEM algorithm with another algorithm called Helmholtz least-squares (HELS) method was created by Wu to solve the Helmholtz integral equation. Possibilities of extending the measurement surface using the analytic continuation was suggested by Valdivia which reduces the measurement aperture restrictions.

The matrices resulting from the inverse boundary element method and the equivalent source model become very ill-conditioned as the system grows larger and larger. The ill-conditioned matrices usually amplify the errors in the measurement when inverted because of the numerical singularities. This error amplification is usually reduced using regularization techniques such as Tikhonov regularization. Hansen provided the details of all the modern methods of regularization. Williams provided a set of regularization methods that are particularly suitable for NAH problems. While the direct regularization methods are used in most of the NAH studies, some of the researchers have adapted the iterative regularization methods in their studies mainly because the iterative methods can handle larger matrices with lesser memory requirement.

In one specific implementation, nearfield acoustic holography is used with a microphone. Conformal and computational methods of NAH have been proven as successful tools to locate and quantify the vibro-acoustic fields. As an inherently nonintrusive technique, the NAH method could possibly emerge as a potential alternative to the present leakage detection methods. Three specific algorithms of NAH are discussed herein, but other algorithms may be used with various implementations. The primary NAH algorithms are Fourier transform (FFT) based NAH, Boundary element method (BEM) based NAH, and Equivalent source model (ESM) based NAH.

The following symbols and variables are used as set forth below:
γ Regularization parameter
$\sigma_i$ Singular values
ω Angular velocity 2π f
$\psi_S$ Any parameter ψ on the source surface
$\psi_H$ Any parameter ψ on the hologram surface
$\psi_V$ Any parameter ψ on the virtual source surface
ρ Density of medium
ξ Local coordinates in the element $A^\dagger$
Pseudo-inverse of any matrix A c
Speed of sound
f Frequency
$f_i$ Filter factors
G Free-space Green's function
k Wave number
$k_x$, $k_y$ Wave numbers in the x and y directions
$N_i$ Shape function
P Acoustic pressure in frequency domain
p̃ Acoustic pressure in time domain
p̂ Acoustic pressure in k, $k_x$ and $k_y$ domain
q Source strength r Position vector
t Time
$v_x$ Particle velocity component in a direction x x Global coordinate Preferred embodiments of the invention place an array of microphones on one side of the structure to be measured and an electroacoustic transducer, such as a loudspeaker on the other side. The speaker emits single frequency tones, multiple frequency tones, or sweeps of frequency/amplitude audio while simultaneously wirelessly communicating phase/amplitude/frequency information. If single frequency tones are used, multiple measurements with tones at different frequencies must be made. There is no fixed range of frequencies that must be spanned by the tones or the sweep, but a range of 100 Hz to 5 kHz is generally preferred to ensure there is sound close at fairly low audio frequencies and fairly high audio frequencies This information is combined with the information picked up from the microphone array to measure the leakage of sound waves through the structure via a NearField Acoustic Holography signal processing technique. The sound leakage information is converted to a static pressure flow equivalent, using basic fluid mechanics, then be easily computed to provide infiltration measurements. Amplifiers and loudspeakers should be capable of producing frequencies below at amplitudes in excess of 60 dB at frequencies below 100 Hz and above 5 kHz. Microphones should have a flat amplitude and phase response over the 100 Hz to 5 kHz range. Microphones should be phase and amplitude matched as much as possible or have amplitude and phase calibration data available to calibrate the microphone output before processing with the NAH algorithms.

If an acoustic pressure field p̃(r, t) obeys the wave equation $$\Delta^2 \tilde{p} - \frac{1}{c^2}\frac{\partial^2 \tilde{p}}{\partial t^2} = 0 \qquad (2)$$

in the space-time domain given by the position vector r and time t, then the nearfield acoustic holography (NAH) methods can be used to estimate the propagation characteristics of the sound field. It is usually very difficult to measure acoustic pressure on the source (S) surface. Therefore, the acoustic pressure p̃($r_H$, t) is usually measured at on a hologram (H) plane which is very close to the source surface. This measurement data is present at N discrete points on the hologram. The Fourier transform of p̃(r, t) is given by:

$$p(r,\omega) = \int_{-\infty}^{\infty} \tilde{p}(r,t)e^{i\omega t}dt \qquad (3)$$

The complex acoustic pressure field p is now in frequency domain. Applying Fourier transform on the wave equation [equation (2)] provides the Helmholtz equation (also called reduced wave equation), $$\Delta^2 p(r,\omega) + k^2 p(r,\omega) = 0 \qquad (4)$$

Here, k is wave number k=ω/c. From Euler's equation, particle velocity $v_n$ can be related to the gradient of acoustic pressure as:

$$v_n(x) = \frac{1}{i\rho c k}\frac{\partial p}{\partial n_s}(x) \qquad (5)$$

where, ρ is the mass density of the medium. At this point, to use the integral form of the Helmholtz equation in the analysis, an important assumption is made that the field obeys Sommerfeld radiation condition, i.e., $$r\left(\frac{\partial p}{\partial n} - ikp\right)$$

vanishes at infinity.

For the Fourier Transform Based NAH, selecting a Green's function (G) that satisfies the homogeneous boundary condition on the source surface, the integral form of Helmholtz equation can be written as:

$$p(x) = -\frac{1}{4\pi}\int\int p(x_s)\frac{\partial G}{\partial n}(x, x_s)d^2 r_s \qquad (6)$$

This equation is known as the Rayleigh's first integral. If the source surface is conformal to the hologram surface, then it is possible to convolute the measured data using the known Green's function on the source surface. The Green's function $G(x, x_S)$ that satisfies the homogeneous Dirichlet boundary condition on the plane $z=z_S$ is given in Maynard et al:

$$G(x, x_s) = \frac{\exp\left[ik\sqrt{(x-x')^2+(y-y')^2+(z-z')^2}\right]}{\sqrt{(x-x')^2+(y-y')^2+(z-z')^2}} - \frac{\exp\left[ik\sqrt{(x-x')^2+(y-y')^2+(z+z'-2z'_S)^2}\right]}{\sqrt{(x-x')^2+(y-y')^2+(z+z'-2z_S)^2}} \quad (7)$$

Therefore, the Rayleigh's first integral [equation (7)] can be written as, $$p(x,y,z) = \iint_{-\infty}^{+\infty} p(x',y',z_S) G'(x-x',y-y',z-z_S) dx'dy' \quad (8)$$

Here, x', y' are dummy variables for integration and G' is the normal derivative of G. The measurement is available only on the hologram surface H. This forms an inverse problem. Evaluating the integral at the hologram surface H:

$$p(x,y,z_H) = \iint_{-\infty}^{+\infty} p(x',y',z_S) G'(x-x',y-y',z_H-z_S) dx'dy' \quad (9)$$

This equation is in two dimensional convolution form, thus $p(x, y, z_S)$ can be obtained using $p(x, y, z_H)$. Two dimensional Fourier transform can be used to convolute the equation. Symbol $\hat{p}$ is used to denote two dimensional spatial Fourier transform.

$$\hat{p}(k_x,k_y,z_H) = \iint_{-\infty}^{+\infty} p(x,y,z_H) e^{i(k_x x + k_y y)} dxdy \quad (10)$$

Applying convolution on equations (9) and (8) and inverting:

$$p(x, y, z) = \mathcal{F}^{-1}\left[\hat{p}(k_x, k_y, z_H)\left(\frac{\hat{G}'(k_x, k_y, z-z_S)}{\hat{G}'(k_x, k_y, z_H-z_S)}\right)\right] \quad (11)$$

Note that the acoustic pressure at the source surface has been eliminated in this equation. This equation (called reconstruction equation) gives the holographic reconstruction $p(x, y, z)$ in three dimensions from the two dimensional measurements $p(x, y, z_H)$. The derivative of G can be calculated from equation (7). Therefore, the two dimensional Fourier transform of G' is given by:

$$\hat{G}'(k_x,k_y,z) = e^{iz\sqrt{k^2-k_x^2-k_y^2}} \quad (12)$$

When $k_x^2+k_y^2 \le k^2$, the kernel in the reconstruction formula, $\hat{G}'(k_x,k_y,z-z_S)$. Therefore, these waves are propagating waves and they change only their phase (not the amplitude) while they propagate. When $k_x^2+k_y^2>k^2$, $e^{-(z-zs)\sqrt{k_x^2+k_y^2+k^2}}$ is now a decaying exponential in z and the waves are referred to as evanescent. The boundary $k_x^2+k_y^2>k^2$ in k space is called radiation circle. By inserting G' in the holographic reconstruction formula, $$p(x,y,z) = \mathcal{F}^{-1}(\hat{p}(k_x,k_y,z_H) e^{ik_z(z\cdots z_S)}) \quad (13)$$

where, $k_z$ is a function of $k_x$ and $k_y$: $k_z = \sqrt{k^2-k_x^2-k_y^2}$. The field gradient $\Delta p$ is related to the particle velocity field $\tilde{v}(r)$ from equation (5). Taking gradient of equation (13) the expression for the particle velocity components $\tilde{v}_x$ in all the three directions, x=x,y,z can be obtained.

$$\tilde{v}_x(x, y, z) = \frac{1}{(2\pi)^2 \rho c} \iint \int_{-\infty}^{+\infty} \hat{p}(k_x, k_y, z_H)[(k_x/k)e^{ik_z(z-z_H)}]e^{i(k_x x + k_y y)} dk_x dk_y \quad (14)$$

The boundary element method (BEM) based NAH algorithm naturally suits the holography analysis (where only the boundary values are known) better than other numerical methods (such as finite element methods) because it reduces the problem dimension by one. Discretization is needed only on the source surface. The solution to the Helmholtz equation (equation (4)) can be found using a surface integration as the Green's function $G(x, x_S)$ is known.

$$\alpha p(x) = \int_{S_k}\left(p(x_S)\frac{\partial}{\partial n_S}G(x,x_S) - G(x,x_S)\frac{\partial}{\partial n_S}p(x_S)\right)dS_S \quad (15)$$

This equation is called Helmholtz integral equation. Here, x and $x_S$ are the field and source points respectively. This equation is of the boundary integral form. The free-space Green's function G is given as:

$$G(x, x_s) = \frac{e^{ikr}}{4\pi r} \quad (16)$$

The parameter $\alpha$ is used, among other reasons, to alleviate the singularity at the corner points (or at the non-smooth nodes).

$$a = \begin{cases} 1, & x \in D, \text{domain not including source surface} \\ 1/2, & x \in S, \text{smooth source surface} \\ \Omega/4\pi, & x \in S, \text{non-smooth source surface} \end{cases}$$

where, $\Omega$ is the solid angle. Changing the Helmholtz integral equation (15) to operator notation provides:

$$\alpha p(x) = (Dp)(x) - \left(S\frac{\partial p}{\partial n_s}\right)(x) \quad (17)$$

The operators are given by the single layer potential, $$\left(S\frac{\partial p}{\partial n_s}\right)(x) = \int_{S_s}\left(G(x,x_s)\frac{\partial p}{\partial n_s}(x_s)\right)dS_s$$

and the double layer potential, $$(Dp)(x) = \int_{S_s}\left(p(x_s)\frac{\partial G}{\partial n_s}(x,x_s)\right)dS_s$$

Quadratic, quadrilateral elements are used in this study. The local coordinates, $\xi \equiv (\xi_1, \xi_2)$, are related to the global coordinates, $x \equiv (x_1, x_2, x_3)$, by the transformation equation:

$$x_i(\xi) = \sum_{i=1}^{L} N_i(\xi) x_{il}, \quad (18)$$

$$i = 1, 2, 3;$$

$$L = 9$$

where, $N_i$ are the shape functions; $x_{il}$ is the $i^{th}$ coordinate of the $I^{th}$ node of the element. Isoparametric approximation is used in this study. Therefore, any field can be approximated in the same way as the coordinates. Therefore, the acoustic pressure at any point in the $m^{th}$ element $p_m$ can be approximated as:

$$p_m(\xi) = \sum_{i=1}^{L} N_i(\xi) p_{ml}, \quad (19)$$

$$m = 1, 2, \ldots, M;$$

$$L = 9$$

where, $p_{ml}$ is the acoustic pressure at the $I^{th}$ node of the $m^{th}$ element and M is the total number of elements. The normal derivative of acoustic pressure $(p_n)_m$ at any point in the $m^{th}$ element proximated in a similar fashion:

$$(p_n)_m(\xi) = \sum_{i=1}^{L} N_i(\xi)(p_n)_{ml}, \quad (20)$$

$$m = 1, 2, \ldots M;$$

$$L = 9$$

The subscript n denotes the normal derivative. Now, the boundary integral equation (15) can be approximated as:

$$\alpha p(x) = \sum_{m=1}^{M} \left[ \left( \int_{\Delta S_m} \frac{\partial G}{\partial n_S}(x, x_S(\xi)) J(\xi) \right) N(\xi) \right) dS_S \right) p_m \right] - \quad (21)$$

$$\sum_{m=1}^{M} \left[ \left( \int_{\Delta S_m} G(x, x_S(\xi)) J(\xi) \right) N(\xi) \right) dS_S \right) (p_n)_m \right]$$

where, $x_s(\xi)$ is calculated using equation (18), $J(\xi)$ is the Jacobian of the transformation, $\Delta S_m$ is the element area, $N(\xi)$ is a row vector with L=9 entries and $p_m$ and $(p_n)_m$ are column vectors with L=9 entries.

Two dimensional Gauss quadrature is used to approximate the elemental integration. Legendre polynomial roots are used to define abscissas and weights of integration points as they are symmetric and appropriate for the elements used here. If there are M elements and N nodes, then equation (21) can be assembled in matrix form.

$$\alpha p(x) = \left( \int_{\Delta S_m} \frac{\partial G}{\partial n_S} JN dS_S \right)^{FS} p^S - \left( \int_{\Delta S_m} GJN dS_S \right)^{FS} p_n^S \quad (22)$$

Or in operator notation:

$$\alpha p(x) = D^{FS} p^S - S^{FS} p_n^S \quad (23)$$

where, $p^S$ and $p_n^S$ are column vectors of size N×1, $D^{FS}$ and $S^{FS}$ are row vectors of size 1×N, F is a field point, S is a source point, and FS is used here to denote the transformation.

Consider the field point is located at the hologram surface H. If there are $N_H$ measurement points in H, then each measurement point will have a row in the assembly matrix. Now, $x \in D_b$, therefore $\alpha = 1$.

$$p^H = D^{HS} p^S - S^{HS} p_n^S \quad (24)$$

where, $p^S$ and $p_n^S$ are column vectors of size N×1, $p^H$ is a column vector of size $N_H \times 1$ and $D^{FS}$ and $S^{FS}$ are matrices of size $N_H \times N$. Similarly, if the field points to be considered to be at the source surface itself, then:

$$\alpha p^S = D^{SS} p^S - s^{SS} p_n^S \quad (25)$$

If the surface is smooth, $\alpha = \frac{1}{2}$, $$\tilde{D}^{SS} p^S = S^{SS} p_n^S \quad (26)$$

where $\tilde{D}^{SS} = D^{SS} - \alpha 1$. 1 is an identity matrix. From equations (23) and (26) $p^S$ or $p_n^S$ can be eliminated. Eliminate $p^S$ is done because the matrix $\tilde{D}^{SS}$ is usually better conditioned and sparse than $S^{SS}$. After eliminating $p^S$:

$$[D^{HS}(\tilde{D}^{SS})^{-1} S^{SS} - S^{HS}] p_n^S = p^H \quad (27)$$

Equation (27) is in the form of $$Ax = p.$$

If the matrix A is well-conditioned, then LU decomposition is used to solve this system of equation to find out $p_n^S$. Then equation (26) can be used to find out $p^S$. After this point, the problem is a forward problem to solve the acoustic pressure distribution at any other surface.

Equivalent source model (ESM) is a rather easier method to implement when compared to the BEM algorithm. A term source strength q is defined as:

$$p(x) = \int_{S_S} (G(x, x_S) q/(x_S)) dS_S \quad (28)$$

$$p_i = \sum_{j=1}^{N} G_{ij} q_i \quad (29)$$

To avoid singularity in the reconstruction, the source strength is estimated on a virtual source surface instead of actual source surface.

$$p_H = G^{HV} q_v \quad (30)$$

Now, this source strength distribution on the virtual surface can be used to calculate the acoustic pressure distribution at the actual source surface without the singularity problem.

$$p^S = G^{VS} q^V \quad (31)$$

The system Ax=p arrived using the BEM and ESM are usually ill-conditioned especially when the matrix is too large. Therefore, the measurement errors and the effects of evanescent waves will be amplified when the matrix A is inverted. The LU decomposition will result in very large coefficients in the inverted matrix. Therefore, the matrix needs to be regularized to reduce the singularities. In this kind of situations, the least square solutions by minimizing the system of equations is the best approach. Consider singular value decomposition (SVD) of matrix A.

$$A = U \Sigma V^H \quad (32)$$

The columns of U and $V^H$ are left and right singular vectors. $\Sigma$ is a diagonal matrix whose diagonal elements $\sigma_i$ are called singular values. U and V are unitary matrices and the $\sigma$ is a diagonal matrix which is very advantageous in computing their inverse individually. Therefore, the pseudo-inverse, $A^\dagger$, can be written as:

$$A^\dagger = V\Sigma^\dagger U^H \quad (33)$$

There are systematic methods to alleviate the singularity in large ill-conditioned systems (details can be seen in the book by Hansen [17]). The regularized solution $x_\gamma$ is given by:

$$x_\gamma = VF\sum{}^\dagger U^H p = \sum_{i=1}^{R} f_i \left(\frac{u_i^H p}{\sigma_i}\right) v_i \quad (34)$$

where, the diagonal matrix F with diagonal entries $f_i$ acts as a filter on the singular matrix. The filter can be chosen in many ways as suggested in prior research. Tikhonov regularization is a well-established direct method and was used in the examples provided below. This method defines the filter factor in terms of a single parameter, $\gamma$, as:

$$f_i = \frac{\sigma_i^2}{\sigma_i^2 + \gamma} \quad (35)$$

By choosing a right value for the parameter $\gamma$, the errors in the solution can be minimized. However, this is done at the cost of losing part of the physical meaning of the data. There are methods to choose the parameter systematically. The three popular methods for the parameter choice are Morozov discrepancy principle, Generalized cross validation (GCV), and L-curve.

GCV is the suitable method when the error in the measurement p is not known exactly.

$$\mathcal{G} = \frac{\|Ax_\gamma - p\|_2^2}{N_H - \mu} \quad (36)$$

where, $$\mu = \sum_{i=1}^{R} f_i.$$

$\gamma$ is optimum when G is minimum.

In an implementation of the present invention, NAH is used to measure both the acoustic pressure and the acoustic velocity on the outside of the enclosure. This is a 2-D measurement that estimates the pressure and velocity at various spots along the enclosure using a microphone array. Thus spatial variation is measured without having to physically move the sensor over the entire enclosure. The pressure is measured inside the enclosure and thus a spatial varying pressure difference can be estimated along with a spatially varying sound velocity. The ratio of surface pressure to velocity is used to separate sound being transmitted through the structure from sound travelling through cracks. Sound traveling through cracks has a much lower ratio of pressure to velocity and so our method can be used to only analyze the sound traveling through cracks as well as identify the location of the cracks. This measurement is done at several frequencies.

The ratio of the pressure difference between interior and exterior to the acoustic velocity in the crack regions is the acoustic transfer impedance of the crack. From the frequency dependent acoustic transfer impedance, the leakage properties of the cracks are estimated. This conversion is described below.

In one implementation, the leakage of the individual cracks is added together to get the total leakage for the section under test.

In one implementation, a key difference in the methodology is the estimation of the acoustic velocity in addition to the acoustic pressure on the outside of the enclosure. It is the combination of having the acoustic velocity and the interior-to-exterior pressure difference that allows one to isolate leaks with a single measurement at a distance and to get the transfer impedance that allows one to estimate the leakage information without resorting to correlation analysis. The microphone array should generally be located as close as possible to the building enclosure and must be located within half a wavelength of the surface where the wavelength of the sound at the frequency under test is the ratio of the speed of sound to frequency.

The acoustic velocity and pressure can be measured in a number of different manners. One embodiment of measurement at a distance is the Nearfield Acoustic Holography, but there are other methods that could be used including the use of a sound intensity probe that is used to measure sound intensity across the outside of the enclosure. One could also use acoustic beamforming to measure the surface pressure and use some other technology to measure the acoustic velocity ABMIS can be used to measure small sections of eventual sealed structures (buildings, aircraft fuselages, hazardous containment enclosures, etc.) during construction to resolve infiltration issues earlier and subsequently at much lower cost/impact to the build effort. This previously unavailable infiltration-detection (and subsequent avoidance) technique could be very valuable in the construction of relatively small sealed structures where infiltration has high cost negative impact (failure, exposure, leakage, etc.). It is clearly far superior to the two techniques currently employed in industry (pressurization testing and tracer gas testing) that are inefficient, inaccurate, and can only be used in finished/sealed structures.

Acquiring Acoustic Properties

Once the acoustic velocity and pressure are measured, they can be used to acquire other acoustic properties necessary to determining the infiltration airflow Q per equation (1). Therefore, infiltration flow it is necessary to calculated the infiltration flow coefficient CL as n the infiltration exponent. A general background is necessary with regard to how cracks are modeled or considered in regard to building infiltration study. In the present invention, velocity and pressure are the known quantities.

Airflow through a crack is governed by the Navier-Stokes equations for Newtonian fluids (Fox, McDonald, & Pritchard, 2004):

$$\frac{\partial \vec{v}}{\partial t} + (\vec{v} \cdot \vec{\nabla})\vec{v} = -\frac{1}{\rho}\vec{\nabla}p + \mu\nabla^2\vec{v} \quad (37)$$

where the fluid density is given by $\rho$, the fluid velocity is given by $\vec{v}$, the fluid pressure is given by p, and the viscosity is given by µ. If steady flow is assume, velocity will not vary in time and Eqn. (37) reduces to $$(\vec{v} \cdot \vec{\nabla})\vec{v} = -\frac{1}{\rho}\vec{\nabla}p + \mu \nabla^2 \vec{v}. \quad (38)$$

Conservation of mass also requires that $$\frac{\partial \rho}{\partial t} + \vec{\nabla} \cdot (\rho \vec{v}) = 0. \quad (39)$$

If the flow is assumed to be incompressible, which is appropriate for infiltration, then density will not change in time, and so Eqn. (39) reduces to $$\vec{\nabla} \cdot \vec{v} = 0. \quad (40)$$

Eqn (38) and (40) are the starting point for our analysis. The velocity field can be broken into components and written as $$\vec{v} = v_x \hat{x} + v_y \hat{y} + v_z \hat{z}. \quad (41)$$

To understand the relationship between pressure drop across a crack and the flow through a crack, consider the simplified geometry shown in FIG. 1A a crack has a length L, a height H, and a depth D. For all analysis that follows, D>>H.

In breaking down a crack into simpler geometries, it can be considered, where height is significantly less than the length and depth, to be a combination of an inlet, a section of Poiseuille flow and an outlet. Examination of two limiting cases is useful in understanding the typical range of values of the exponent n in Eqn. (1). The first case is fully developed flow where the length and depth of the crack are extremely large compared to the crack height H, commonly called Poiseulle flow which yields n=1.0. The second case is flow through a thin orifice, the inlet and the outlet, which yields n=0.5. One can assume that the pressure gradient driving the flow is a gradient only in the x direction which means that $$\nabla p = \frac{\partial p}{\partial x}. \quad (42)$$

A first step in determining the infiltration exponent is to determine the portion of the crack assumed to be Poisuell flow. Thus, when the depth of the crack D and length of the crack L are much larger than the height H and the flow is primarily in the x direction. Assuming the length of the crack L and depth D are is infinite, flow will be fully developed in the x direction and there will be no variation in the y direction. By symmetry arguments, the velocity will only vary as a function of z direction and thus the velocity field reduces to $$\vec{v} = v_x(z)\hat{x}. \quad (43)$$

With the velocity in this form, $$(\vec{v} \cdot \vec{\nabla})\vec{v} = v_x(z)\frac{\partial}{\partial x}v_x(z) = 0 \quad (44)$$

and thus Eqn (38) reduces to $$\frac{1}{\rho}\frac{\partial p}{\partial x} = \mu \frac{\partial^2 v_x(z)}{\partial z^2}. \quad (45)$$

Eqn. (45) can then be integrated twice in z to yield $$v_x(z) = \frac{1}{2\rho\mu}\frac{dp}{dx}z^2 + C_1 z + C_2. \quad (46)$$

Using the no-slip boundary conditions ($v_x$=0) on the walls of the crack (z=0 and z=H), the constants can be evaluated to yield $$v_x(z) = \frac{1}{2\rho\mu}\frac{dp}{dx}(z^2 - \text{H}z). \quad (47)$$

The total volume flow rate of fluid through the crack, Q, is given by integrating the velocity across the crack face $$Q = \iint_{y,z} v_x dydz = \int_0^D \int_0^H \frac{1}{2\rho\mu}\frac{dp}{dx}(z^2 - \text{H}z)dydz = -\frac{DH^3}{12\rho\mu}\frac{dp}{dx}. \quad (48)$$

For a given pressure difference across the crack, Δp, the pressure gradient is given by $$\frac{\partial p}{\partial x} = -\frac{\Delta p}{L}, \quad (49)$$

with the negative sign appearing because the pressure gradient is opposite the actual direction of flow. Combining Eqn. (48) and Eqn. (49) provides that the pressure drop created by viscous flow Q through a through a long crack, ignoring end effects, will be $$\Delta p = \frac{12\rho\mu L}{DH^3}Q. \quad (50)$$

Eqn. (50) shows the flow exponent, n, and flow coefficient, $C_L$, to put this into the power law form of Eqn. (1) are given by $$n = 1 \quad (51)$$
$$C_L = \frac{DH^3}{12\rho\mu L}.$$

Figure 1B:
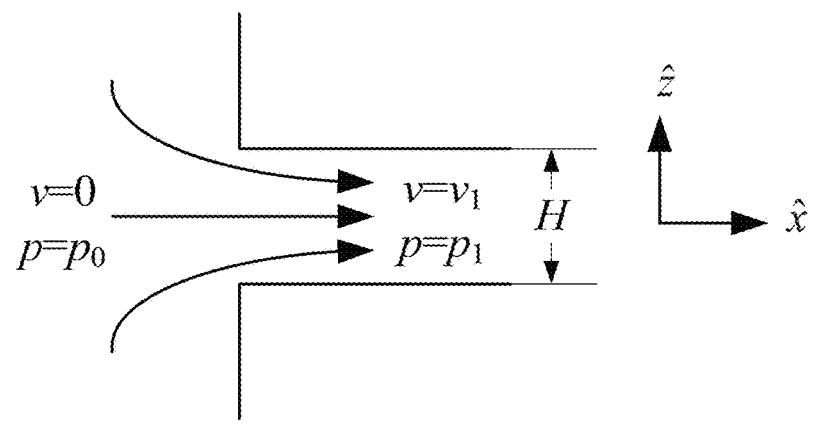
FIG. 1B illustrates geometry for studying flow into the inlet of the crack of height H of FIG. 1A.

As a second step, to understand the pressure drop flow relation at the inlet (and by correlation the outlet), the same assumption is made that the inlet (and outlet) is of a crack that is very long and very deep. A cross sectional diagram is shown in FIG. 1B. Well away from the inlet, the pressure is $p_0$, and the flow velocity is essentially zero. Just within the crack, the flow velocity has increased to $v_1$ and the pressure has dropped to $p_1$. Over a short distance, viscous losses are negligible and the pressure drop will be completely from the force required to accelerate the fluid from a velocity of 0 to $v_1$.

While the flow into the inlet is quite complex, it still follows Bernoulli's theorem, a form of conservation of energy, which states that along any streamline the quantity $$\frac{1}{2}\|\vec{v}\|^2 + \frac{p}{\rho} \tag{52}$$

is constant. Applying Eqn. (52) to a streamline that starts far from the crack where the flow velocity is zero and the pressure is $p=p_0$ and the flow accelerates to a velocity $v_1$ and a pressure $p_1$ inside the inlet yields the equation $$\frac{p_0}{\rho} = \frac{1}{2}v_1^2 + \frac{p_1}{\rho}. \tag{53}$$

Identifying $\Delta p = p_0 - p_1$ and noting that the volume rate of flow will be $Q = HDv_1$ one can write $$\Delta p = \frac{1}{2}\rho v_1^2 = \frac{1}{2}\frac{\rho Q^2}{HD}. \tag{54}$$

This equation can be inverted to yield $$Q = \sqrt{\frac{2}{\rho}} HD \Delta p^{0.5}, \tag{55}$$

from which the flow exponent, n, and flow coefficient, $C_L$, are given by $$n = 0.5 \tag{56}$$

$$C_L = DH\sqrt{\frac{\Delta p}{\rho}}.$$

An outlet has essentially the same physics as an inlet and by Bernoulli's theorem will end up having the same relationship pressure-flow as Eqn. (54).

Having determined the flow exponent for the components of the crack as well as the flow coefficient (as a function of other parameters of the system), a simple model for a complete crack can be considered by combination of an inlet, outlet, and a section of Poiseuille flow as each was described above. Thus using Eqn. (54) and Eqn. (50) a first approximation to the relation between pressure drop and volume of flow through a crack will be $$\Delta p = \frac{1}{2}\frac{\rho Q^2}{D^2 H^2} + \frac{12\rho\mu L}{DH^3}Q + \frac{1}{2}\frac{\rho Q^2}{D^2 H^2} = \frac{12\rho\mu L}{DH^3}Q + \frac{\rho Q^2}{D^2 H^2}. \tag{57}$$

Because of the approximations that were made to the inlet and outlet flow and the assumption of fully developed flow within the crack, modifications to Eqn. (57) are necessary. A more general form of Eqn. (57) introduced by Walker (Walker, Wilson, & Sherman, 1997) is $$\Delta p = AQ + BQ^2 \tag{58}$$

where the coefficients A and B are typically developed through analytic analysis (as above), computational analysis (often using computational fluid dynamics), or measurements. Comparison of Eqns 57 and 58 shows that for our simple slit, the coefficients and A and B are $$A = \frac{12\rho\mu L}{SH^2} \tag{59}$$

and $$B = \frac{\rho}{S^2}$$

where $S = DH$ is the cross sectional area of the crack.

Eqn. 58 is not in the power law form of Eqn. 1. It has been posited by prior researchers that the power law form is more useful, especially when ambient temperature and pressure corrections need to be made. When measured data at several different pressures are available, Eqn. 58 can be cast into a power law form of Eqn. 1 through a least squares fit of Eqn. 1 to Eqn. 58 for $C_L$ and n.

In addition to the above method using $C_L$ and n can be estimated through other means, in particular, if the alternative form of $Q(\Delta p)$ is known, one can estimate n in the following manner:

$$Q = C_L(\Delta P)^n \tag{60}$$

$$\frac{dQ}{d\Delta p} = nC(\Delta p)^{n-1} = n\frac{Q}{\Delta p} \tag{61}$$

and therefore $$n = \frac{dQ}{d\Delta p}\frac{\Delta p}{Q}. \tag{62}$$

Inverting Eqn. (58) provides an alternative equation for Q and terms of $\Delta p$ $$Q = \frac{\sqrt{A^2 + 2B\Delta p} - A}{2B}. \tag{63}$$

Using Eqn. 62 in Eqn. 61 and simplifying provides:

$$n = \frac{1}{2}\left(\frac{A}{\sqrt{A^2 + 4B\Delta p}} + 1\right). \tag{64}$$

Eqn. 63 is not independent of $\Delta p$, but such is not seen in the limits of Poiseuille flow (B→0), n→1 and in the limit of inlet dominated flow (A→0), n→0.5 as expected. Using Eqns 28 and 24:

$$C_L = \Delta p^{-n}\frac{\sqrt{A^2 + 4B\Delta p} - A}{2B}. \tag{65}$$

If one can find the coefficients A and B, the flow coefficient $C_L$ and flow exponent n can be estimated by use of a standardized reference pressure difference.

The coefficients A and B can be estimated from acoustic impedance The acoustic impedance of slits and cracks has been studied by many authors (Sivian, 1935; Wood & Thurston, 1953) and can be calculated. The acoustic transfer impedance of a rectangular slit of length L, height H, depth D, and cross sectional area S=DH at a frequency f is given by $$Z = \frac{j\omega\rho L}{S} \frac{(1+j)Y}{\tan((1+j)Y) - (1+j)Y} \quad (66)$$

where $=\sqrt{-1}$, $\omega=2\pi f$, and the ratio of slit thickness to viscous penetration depth, Y, is given by $$Y = H\sqrt{\frac{\omega\rho}{8\mu}}. \quad (67)$$

The low frequency ($\omega \to 0$) limit of Eqn. 68 is $$Z_0 = Z|_{\omega \to 0} = 12\frac{\mu L}{SH^2} + j\omega\frac{6\rho L}{5S} \quad (68)$$

The high frequency ($\omega \to \infty$) limit of Eqn. 68 is $$Z_\infty = Z|_{\omega \to \infty} \sqrt{2\mu\rho\omega}\frac{L}{SH} + j\omega\frac{\rho L}{S} \quad (69)$$

The real part of Eqn. 70 can be identified directly as the infiltration coefficient A and can thus be measured directly from a low frequency acoustic impedance measurement $$A = Re\{Z|_{\omega \to 0}\}. \quad (70)$$

The coefficient $B = \mu/S^2$ depends only on $\rho$ and crack cross-sectional area S and so if an estimate of S is available, the coefficient B can be directly estimated. The area S could be estimated from analysis of the surface acoustic measurements made using acoustic holography above.

The coefficient $B = \mu/S^2$, cannot be directly identified from impedance measurements; however, if one is able to estimate the crack length L by some other means, such as time delay analysis of reflections in the crack or crack cavity resonance analysis (Munjal, 1987), then $$B = \frac{25}{36\rho L^2} Im\{Z|_{\omega \to \infty}\}^2. \quad (71)$$

The coefficients A and B were estimated directly from impedance measurements through comparison of analytics expressions developed from idealizations. Real world cracks will tend to be more complicated and the analytic expressions may not be very accurate. Alternatively, one can develop better relationships between the static flow coefficients and acoustic impedance through correlations of static flow relationships and acoustic impedance as calculated through computational fluid dynamics (CFD).

The analysis above does show that A is closely related to the low frequency limit of the real part of the transfer impedance and B can be related to the imaginary part of the transfer impedance. Correlation coefficients relating the transfer impedance computed through CFD, $Z_{CFD}(\omega)$, and the coefficients $A_{CFD}$ and $B_{CFD}$ computed by CFD can be defined as $$CC_A = \frac{A_{CFD}}{\int_{\omega_{min}}^{\omega_{max}} Re\{Z_{CFD}(\omega)\}d\omega} \quad (72)$$

and $$CC_B = \frac{B_{CFD}}{\int_{\omega_{min}}^{\omega_{max}} Im\{Z_{CFD}(\omega)\}d\omega} \quad (73)$$

where $\omega_{min}$ and $\omega_{max}$ are selected by the user to match the actual range of frequencies used to measure the transfer impedance, $Z_m$. Then, the coefficients of A and B of the actual cracks are found as $$A = CC_A \int_{\omega_{min}}^{\omega_{max}} Re\{Z_m(\omega)\}d\omega \quad (74)$$

and $$B = CC_B \int_{\omega_{min}}^{\omega_{max}} Im\{Z_m(\omega)\}d\omega. \quad (75)$$

EXAMPLES

This section describes experiments regarding certain implementations of the present invention. To qualify various algorithms of NAH a loudspeaker experiment was designed. A sub-woofer of diameter 10 inches was placed in an anechoic chamber located at IIT Fluid Dynamics Research Center. Simultaneous measurement at all the points in the hologram is not necessary for the frequency domain NAH analysis that are used in this study. Therefore, a single microphone fixed on a motorized traverse (shown in FIG. 2(a)) is used to record the sound signal on a two dimensional surface (which is called hologram surface). The hologram surface is located at distance 0.5 inches from the source. A quarter inch, B & K (model 4338) microphone is used here with appropriate power supply and filter. 204800 samples are acquired using an NI DAQ module at a rate of 100 kHz. The measurement aperture is 28 in×28 in rectangle with 113×113 measurement points (0.25 in between adjacent measurement points). A sine signal of single frequency is generated in Labview and supplied through an NI DAC to a power amplifier. The amplified signal runs the loudspeaker. Frequencies considered for this test are 317 Hz, 1098 Hz, and 5004 Hz.

Figure 2:
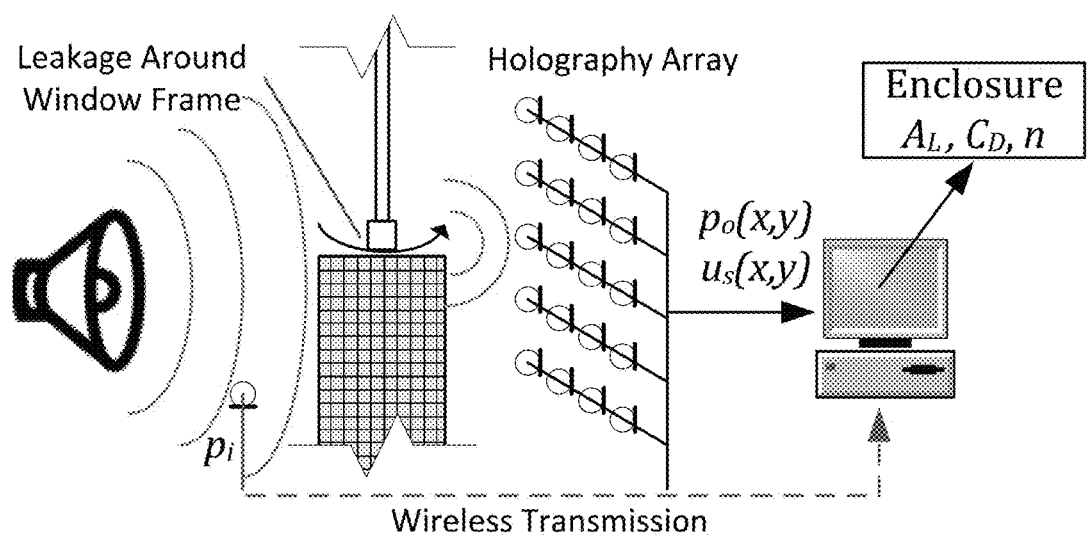
FIG. 2 is a basic diagram of the ABIMS system. Transmission of sound waves is measured with a nearfield acoustic holography array. These data are converted to infiltration estimates.
Figure 3A:
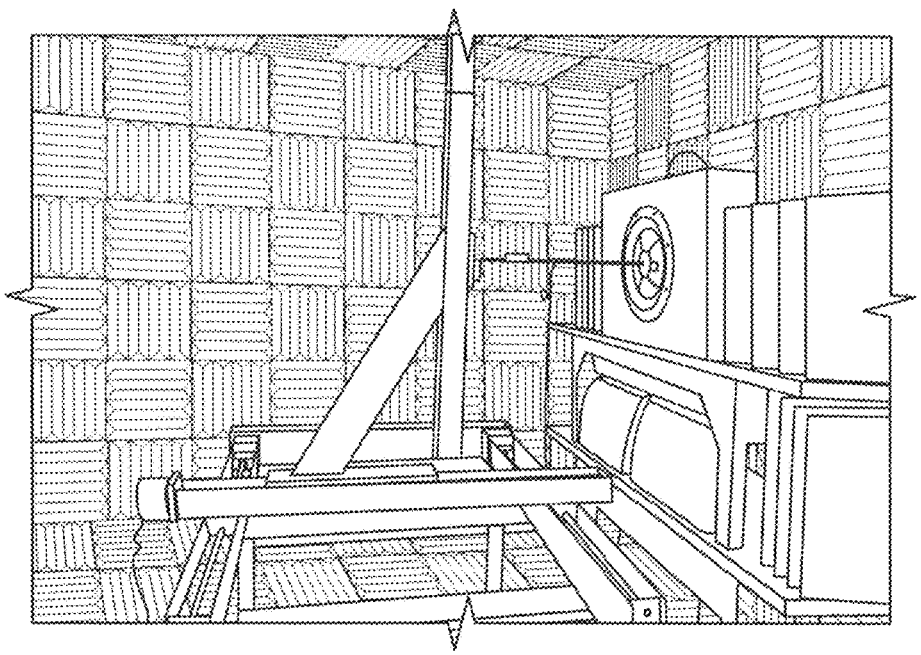
FIGS. 3A-B illustrates a traversing single microphone setup for (a) qualification test (b) building block measurement.
Figure 3B:
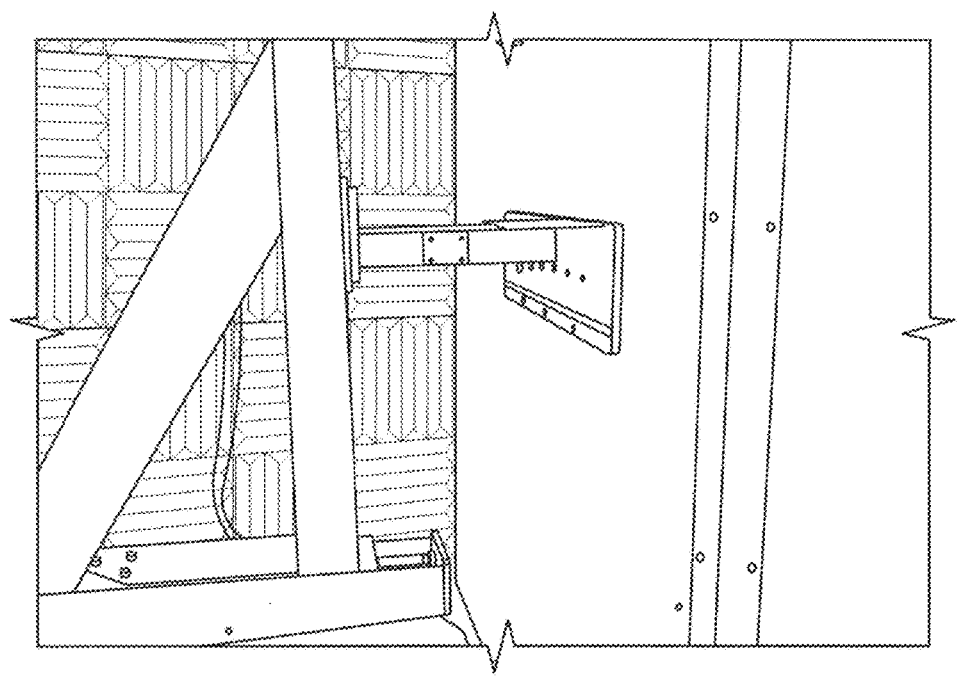
Figure 3C:
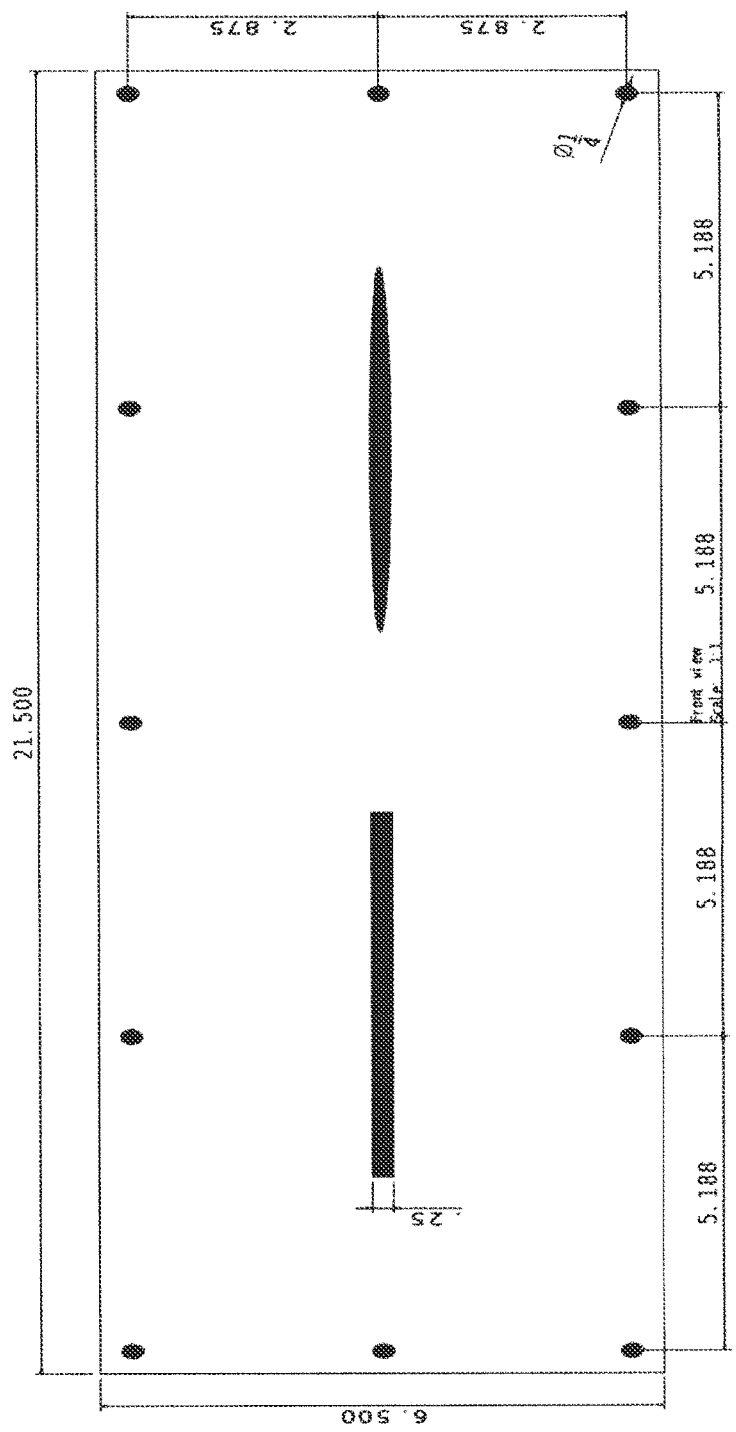
FIG. 3C-D illustrate the two inserts used in the described experiments to simulate a leakage area of a building.
Figure 3D:
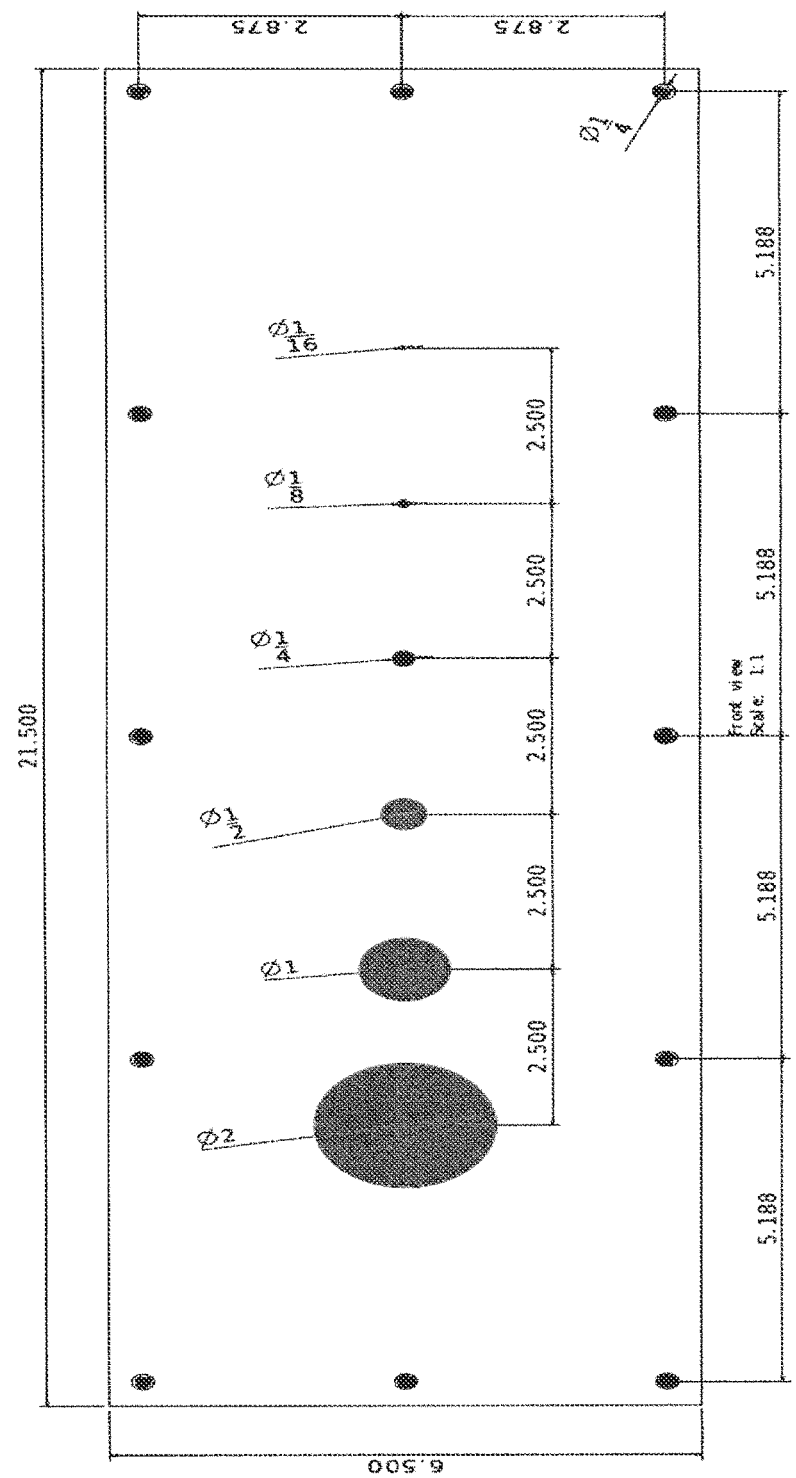
Figure 16:
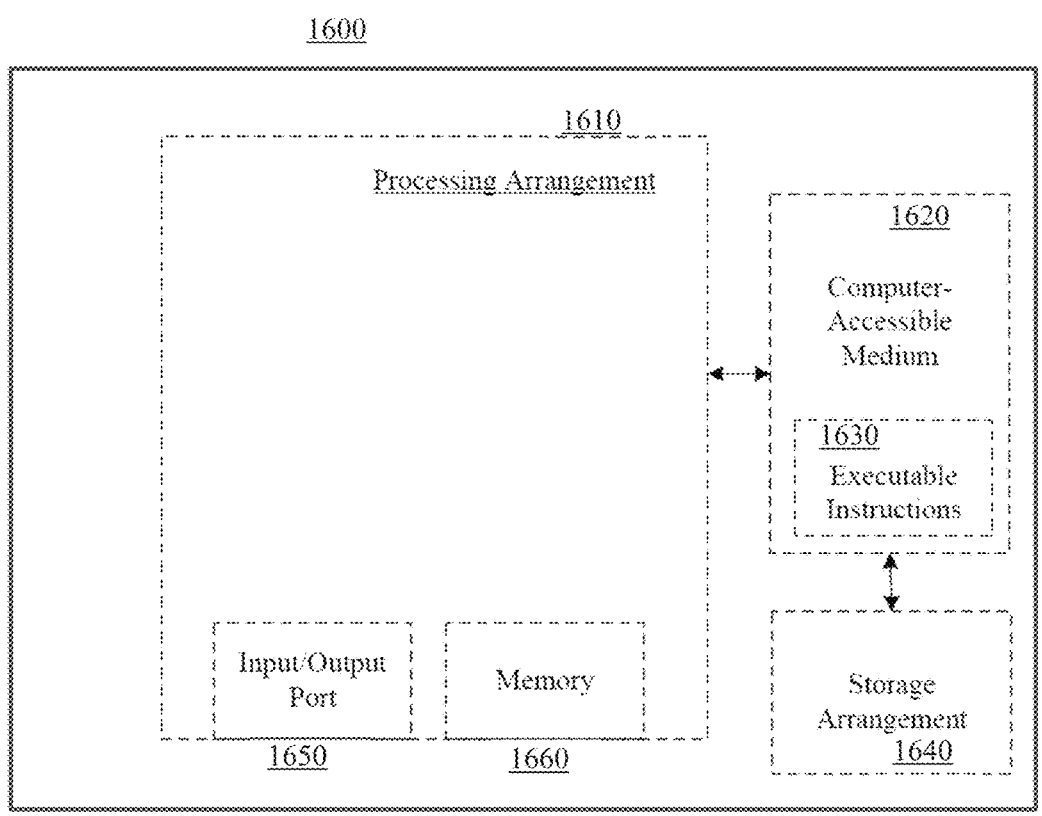
FIG. 16 is an illustration of a computer implementation of an embodiment.

For the leakage detection experiment, a wooden model of a building is built with the dimensions 68"×50"×32". This building model has a 20"×6" opening which can hold an insert plate with specified slots on it. These slots can be considered as known leakage areas. The loudspeaker is mounted inside the model. The measurement is performed in the same way as the loudspeaker experiment. The hologram surface is 0.5 in away from the building surface. This setup is shown in FIG. 2b). FIG. 4 shows the two different insert plates used in these examples. The insert plates are of dimensions 20"×6" and made up of acrylic glass material.

The insert I has a rectangular slot and an elliptical slot each of width 6 in and maximum height of 0.25 in. Insert II has circular holes of various diameters ranging from 2 in to 1/16 in.

The computer programs for FFT, BEM and ESM based methods were developed in FORTRAN and compiled using GNUFORTRAN compiler. The results were plotted using MATLAB.

As mentioned in the previous section, to check the algorithms a loudspeaker experiment was used. The acoustic pressure measured on the hologram is used to reconstruct the acoustic pressure and particle velocity field on the source surface. FIG. 4 shows the contours of acoustic pressure on the source surface (which is a planar surface very close the speaker surface) for the input frequency of 5004 Hz. The results show that all the three algorithms are able to detect the sources reasonably well. The predicted pressure levels are a little different for each algorithm due to the different numerical approximations used in them. However, when converted to log (dB) scale these differences would not make so much sense. For the other two frequencies, the reconstruction results were similar (not shown here).

The dynamic range for all the plots shown in this section are chosen as 65 percent of the maximum value. The calculated acoustic pressure and particle velocity are complex quantities. Therefore, the absolute value is used here to plot.

The sound leaks through the same locations as the air. Therefore, sound is generated inside the building model and the acoustic pressure is measured on hologram surface and it is inverse reconstructed to the building model surface to detect the known leakage locations. Diffraction characteristics depends on the frequency/wavelength of the propagating sound wave. Also, the NAH works very well when the areas dominated by evanescent waves are minimum (the evanescent cut-off is also based on frequency/wave number). Therefore, three different input frequencies are chosen for this study (5004, 1098 and 317 Hz) and the results are presented below.

Higher Input Frequency

FIG. 5 shows the acoustic pressure fields on the surface of insert I calculated using various algorithms. The FFT algorithm is based on the Rayleigh's integral and the ESM theory neglects the dipole term completely. Therefore, these two algorithms are supposed to be inferior to the BEM algorithm in terms of accuracy. It is clear from FIG. 5 that BEM gives the closer idea of the leakage location. However, the solution lacks smoothness compared to the ESM and FFT solutions. This non-smoothness in the solution is expected when using the quadratic approximation in the BEM algorithm as explained in the prior art. However, when using linear approximation the solution could lose accuracy. FIG. 6 shows the acoustic pressure field reconstructed on the surface of insert II. All the algorithms are able to detect the larger source. However, none of the algorithms are able to resolve the smaller sources on the insert. This could be due to the domination of the larger source in the field. Another set of experiments must be conducted with smaller sources exclusively in the absence of larger sources to find out if at all a given algorithm is able to detect a source of particular size.

FIGS. 7 and 8 show the calculated particle velocity field on insert I and II respectively. The contours looks similar to the acoustic pressure contours shown in FIGS. 5 and 6 because the particle velocities are basically calculated using the acoustic pressure field.

Lower Input Frequency

The lower frequency chosen in this study is 317 Hz. FIGS. 9 and 10 show the acoustic pressure distribution calculated using various algorithms on the surfaces of insert I and insert II respectively. The localizing effect is much worse for this frequency when compared with the higher frequency. NAH methods have inherent problem with the evanescent waves. For the lower frequency analysis, most of the domain contains evanescent components when compared to the higher frequency analysis. Therefore, it is confirmed that the higher the wave number, better the reconstructed result. FIGS. 11 and 12 shows the particle velocity distribution for the same frequency. One can easily notice that the particle velocity values are not realistic. These higher values of pressure and particle velocities appear in the NAH calculation because the errors in the measurement grow exponentially during inverse calculation when the domain is dominated by evanescent waves. There are ways to reduce this effect which will be discussed below.

Intermediate Input Frequency

Intermediate frequency case (1098 Hz) response is in between higher and lower frequency cases. For this case, not all the results are shown here. A sample can be seen in FIG. 13. FIG. 13 shows the acoustic pressure and particle velocity distribution on the surface of insert II. The shown result is obtained using ESM algorithm.

Effect of Regularization and Resolution

As mentioned earlier, the evanescent components can be minimized in the calculation using various techniques. The regularization technique is well known in some cases to alleviate this error. FIG. 14 shows the regularized ESM result on the surface of insert I for the lower frequency case. GCV method is used here to select the Tikhonov parameter. It is well known that sometimes GCV over-predicts the regularization parameter. In the present case also it is clear that the GCV applies over-regularization. Therefore, the pressure and particle velocity values are predicted very low. Also, the localization effect is lost in the contour.

Bai suggests reducing the resolution increases the accuracy of reconstructed values. The resolution is suggested to be double the distance between hologram and source. However, due to the scale of the present model, this suggested resolution is not desirable. Therefore, the resolution is reduced from $\Delta x=0.25$ in to $\Delta x=0.5$ in and the sample results can be found in FIG. 15. FIG. 15 shows the particle velocity distribution on the surface of insert I. The values are more realistic than the higher resolution results.

From the results presented above, it is evident that the NAH algorithms have the potential to be used in the future to detect leakages. Higher input frequencies give better results because of their higher wave numbers as evanescent waves appear only in the regions where $k^2 < k_x^2 + k_y^2$. FFT and ESM algorithms arrive at similar results in most of the cases. The BEM results are nonsmooth because of the quadratic approximation used. Tikhonov regularization could be an effective method to reduce the error by avoiding some of the singular values. However, choosing the proper Tikhonov parameter is a difficult task and generalized cross validation is not performing very well for the present geometry. Therefore, modern methods like L-curve criterion must be tried for this geometry in the future. Reducing the resolution usually helps to increase the accuracy and the present results confirm that.

The foregoing description of illustrative embodiments has been presented for purposes of illustration and of description. It is not intended to be exhaustive or limiting with respect to the precise form disclosed, and modifications and variations are possible in light of the above teachings or may be acquired from practice of the disclosed embodiments. It is intended that the scope of the invention be defined by the claims appended hereto and their equivalents.

What is claimed is:

1. A method of detecting leakage comprising:
    emitting sound at a frequency and having a wavelength from an electroacoustic transducer positioned within a structure;
    measuring, with a microphone positioned internal to the structure, an internal pressure of the emitted sound within the structure;
    positioning a holographic array of microphones external to the structure, the array of microphones positioned, relative to the structure, within half of the wavelength of the emitted sound;
    measuring, by nearfield acoustic holography with the array of microphones, external pressure and external velocity of the sound at discrete points on the exterior of the structure;
    determining at each of the points an interior-to-exterior acoustic transfer impedance; and
    identifying, based upon the determined acoustic transfer impedance, the size and location of a leak in the structure.

2. The method of claim 1, wherein detecting sound comprises detecting sound by nearfield acoustic holography.

3. The method of claim 2, wherein detecting sound by nearfield acoustic holography comprises positioning a holographic array comprising a plurality of microphones positioned external to the structure.

4. The method of claim 3 wherein determining the leak comprises applying a nearfield acoustic holography algorithm selected from the group consisting of Fourier transform (FFT) based NAH, Boundary element method (BEM) based NAH, and Equivalent source model (ESM) based NAH.

5. The method of claim 1, wherein detecting sound comprises detecting sound by a sound intensity probe positioned external to the structure.

6. The method of claim 1, wherein external pressure is measured by acoustic beamforming.

7. The method of claim 1, further comprising determining an acoustic transfer impedance of the leak.

8. The method of claim 1, wherein determining the leak in the structure comprises determining at least one acoustic property based upon the measured internal pressure, external pressure, and velocity.

9. The method of claim 1, comprising determining a plurality of leaks.

10. The method of claim 9, further comprising determining the leakage for a section of the structure by adding the determined plurality of leaks corresponding to the section.

11. The method of claim 1, wherein determining a leak comprises determining the ratio of pressure to velocity for a plurality of sections.

12. The method of claim 1, wherein the emitted sound is within the range of 100 Hz to 5 kHz and at least 60 dB.

13. A system for detecting leakage of a structure, comprising:
    an electroacoustic transducer positioned inside the structure and configured to emit an acoustic wave having a phase, frequency and amplitude;
    an interior transducer located inside the structure and in communication with a computer to provide the phase, frequency, and amplitude of the emitted acoustic wave; and
    an external acoustic transducer system configured to detect acoustic pressure and acoustic velocity on the outside of the structure within a distance of half of a wavelength of the emitted acoustic wave.

14. The system of claim 13, wherein the acoustic transducer system comprises an acoustic holography microphone array configured to receive the acoustic waves on the outside of the structure and in communication with the computer.

15. The system of claim 14, wherein the acoustic holography array comprises an array of pressure transducers.

16. The system of claim 14, wherein the acoustic holography array is a nearfield acoustic holography array.

17. A computer system for leakage detection comprising:
    a loudspeaker configured to emit an acoustic wave having a phase, frequency and amplitude within a structure, an internal microphone positioned within the structure and in communication with a computer to provide the phase, frequency, and amplitude of the emitted acoustic wave;
    a microphone array positioned outside of the structure within half of a wavelength of the emitted acoustic wave and configured to receive the acoustic wave, the microphone array in communication with the computer providing acoustic pressure data to the computer;
    the computer including a processor and a tangible computer-readable medium operatively connected to the processor and including computer code configured to:
    determine leakage from the array acoustic velocity and pressure data associated with each of a plurality of points.

18. The system of claim 17, wherein the microphone array comprises an array of pressure transducers.

19. The system of claim 17, wherein the microphone array is a nearfield acoustic holography array.

* * * * *